United States Patent
Drews et al.

(10) Patent No.: US 9,814,522 B2
(45) Date of Patent: Nov. 14, 2017

(54) APPARATUS AND METHODS FOR ABLATION EFFICACY

(75) Inventors: Michael J. Drews, Palo Alto, CA (US); Bryan Wylie, San Jose, CA (US); Leslie Oley, Palo Alto, CA (US); Vahid Saadat, Atherton, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 875 days.

(21) Appl. No.: 13/081,363

(22) Filed: Apr. 6, 2011

(65) Prior Publication Data

US 2012/0059366 A1 Mar. 8, 2012

Related U.S. Application Data

(60) Provisional application No. 61/321,471, filed on Apr. 6, 2010.

(51) Int. Cl.
*A61B 18/14* (2006.01)
*A61B 18/00* (2006.01)
(Continued)

(52) U.S. Cl.
CPC ........ *A61B 18/1492* (2013.01); *A61B 18/082* (2013.01); *A61B 2018/0038* (2013.01);
(Continued)

(58) Field of Classification Search
CPC .... A61B 2218/00–2218/005; A61B 2218/007; A61B 1/0008–1/00094; A61B 2018/00214; A61B 2018/0022; A61B 2018/00232; A61B 1/00082; A61B 1/00101; A61B 2018/00273; A61B 2018/00351; A61B 2018/00357; A61B 2018/00375; A61B 2018/0038;
(Continued)

(56) References Cited

U.S. PATENT DOCUMENTS 623,022 A 4/1899 Johnson
2,305,462 A 12/1942 Wolf
(Continued)

FOREIGN PATENT DOCUMENTS

DE 10028155 A1 12/2000
EP 0283661 9/1988
(Continued)

OTHER PUBLICATIONS

Avitall, "A Catheter System to Ablate Atrial Fibrillation in a Sterile Pericarditis Dog Model", *PACE*, vol. 17, p. 774, 1994.
(Continued)

*Primary Examiner* — Jaymi Della
*Assistant Examiner* — Eunhwa Kim

(57) ABSTRACT

Apparatus and methods for ablation efficacy are described herein where a hood having a deployable elongated feature can extend beyond a distal face of the hood. The elongated feature can channel the energy to the deeper regions within the tissue (such as trabeculated regions or other tissue structures) such that the energy can be delivered to the target tissue despite small or large irregularities in the target tissue surface (or region) and/or changes in the relative distances between the hood and the target tissue.

20 Claims, 23 Drawing Sheets

(51) Int. Cl.
   *A61B 18/08* (2006.01)
   *A61B 90/00* (2016.01)

(52) U.S. Cl.
   CPC ............ *A61B 2018/00273* (2013.01); *A61B 2018/00351* (2013.01); *A61B 2018/00375* (2013.01); *A61B 2018/00577* (2013.01); *A61B 2018/00982* (2013.01); *A61B 2018/1472* (2013.01); *A61B 2018/1475* (2013.01); *A61B 2090/0436* (2016.02); *A61B 2090/0481* (2016.02); *A61B 2218/002* (2013.01)

(58) Field of Classification Search
   CPC  A61B 2018/00577; A61B 2018/00982; A61B 18/082; A61B 18/1492
   USPC .......................................................... 606/34
   See application file for complete search history.

(56) References Cited

U.S. PATENT DOCUMENTS

| | | |
|---|---|---|
| 3,874,388 A | 4/1975 | King et al. |
| 4,175,545 A | 11/1979 | Termanini |
| 4,326,529 A | 4/1982 | Doss et al. |
| 4,445,892 A | 5/1984 | Hussein et al. |
| 4,470,407 A | 9/1984 | Hussein et al. |
| 4,569,335 A | 2/1986 | Tsuno |
| 4,576,146 A | 3/1986 | Kawazoe et al. |
| 4,615,333 A | 10/1986 | Taguchi |
| 4,619,247 A | 10/1986 | Inoue et al. |
| 4,676,258 A | 6/1987 | Inokuchi et al. |
| 4,681,093 A | 7/1987 | Ono et al. |
| 4,709,698 A | 12/1987 | Johnston et al. |
| 4,710,192 A | 12/1987 | Liotta et al. |
| 4,727,418 A | 2/1988 | Kato et al. |
| 4,784,133 A | 11/1988 | Mackin |
| 4,848,323 A | 7/1989 | Marijnissen et al. |
| 4,911,148 A | 3/1990 | Sosnowski et al. |
| 4,914,521 A | 4/1990 | Adair |
| 4,943,290 A | 7/1990 | Rexroth et al. |
| 4,950,285 A | 8/1990 | Wilk |
| 4,957,484 A | 9/1990 | Murtfeldt |
| 4,961,738 A | 10/1990 | Mackin |
| 4,976,710 A * | 12/1990 | Mackin ........................... 606/15 |
| 4,991,578 A | 2/1991 | Cohen |
| 4,994,069 A | 2/1991 | Ritchart et al. |
| 4,998,916 A | 3/1991 | Hammerslag et al. |
| 4,998,972 A | 3/1991 | Chin et al. |
| 5,057,106 A | 10/1991 | Kasevich et al. |
| 5,090,959 A | 2/1992 | Samson et al. |
| 5,123,428 A | 6/1992 | Schwarz |
| RE34,002 E | 7/1992 | Adair |
| 5,171,259 A | 12/1992 | Inoue |
| 5,281,238 A | 1/1994 | Chin et al. |
| 5,282,827 A | 2/1994 | Kensey et al. |
| 5,306,234 A | 4/1994 | Johnson |
| 5,313,943 A | 5/1994 | Houser et al. |
| 5,330,496 A | 7/1994 | Alferness |
| 5,334,159 A | 8/1994 | Turkel |
| 5,334,193 A | 8/1994 | Nardella |
| 5,336,252 A | 8/1994 | Cohen |
| 5,339,800 A | 8/1994 | Wilta et al. |
| 5,348,554 A | 9/1994 | Imran et al. |
| 5,353,792 A | 10/1994 | Lubbers et al. |
| 5,370,647 A | 12/1994 | Graber et al. |
| 5,373,840 A | 12/1994 | Knighton |
| 5,375,612 A | 12/1994 | Cottenceau et al. |
| 5,385,148 A | 1/1995 | Lesh et al. |
| 5,403,326 A | 4/1995 | Harrison et al. |
| 5,405,376 A | 4/1995 | Mulier et al. |
| 5,421,338 A | 6/1995 | Crowley et al. |
| 5,431,649 A | 7/1995 | Mulier et al. |
| 5,453,785 A | 9/1995 | Lenhardt et al. |
| 5,462,521 A | 10/1995 | Brucker et al. |
| 5,471,515 A | 11/1995 | Fossum et al. |
| 5,498,230 A | 3/1996 | Adair |
| 5,505,730 A | 4/1996 | Edwards |
| 5,515,853 A | 5/1996 | Smith et al. |
| 5,527,338 A | 6/1996 | Purdy |
| 5,549,603 A | 8/1996 | Feiring |
| 5,558,619 A | 9/1996 | Kami et al. |
| 5,571,088 A | 11/1996 | Lennox et al. |
| 5,575,756 A | 11/1996 | Karasawa et al. |
| 5,575,810 A | 11/1996 | Swanson et al. |
| 5,584,872 A | 12/1996 | LaFontaine et al. |
| 5,591,119 A | 1/1997 | Adair |
| 5,593,422 A | 1/1997 | Muijs Van de Moer et al. |
| 5,593,424 A | 1/1997 | Northrup, III |
| 5,672,153 A | 9/1997 | Lax et al. |
| 5,676,693 A | 10/1997 | LaFontaine |
| 5,681,308 A | 10/1997 | Edwards et al. |
| 5,695,448 A | 12/1997 | Kimura et al. |
| 5,697,281 A | 12/1997 | Eggers et al. |
| 5,697,882 A | 12/1997 | Eggers et al. |
| 5,709,224 A | 1/1998 | Behl et al. |
| 5,713,907 A | 2/1998 | Hogendijk et al. |
| 5,713,946 A | 2/1998 | Ben-Haim |
| 5,716,321 A | 2/1998 | Kerin et al. |
| 5,722,403 A | 3/1998 | McGee et al. |
| 5,725,523 A | 3/1998 | Mueller |
| 5,746,747 A | 5/1998 | McKeating |
| 5,749,846 A | 5/1998 | Edwards et al. |
| 5,749,890 A | 5/1998 | Shaknovich |
| 5,754,313 A | 5/1998 | Pelchy et al. |
| 5,766,137 A | 6/1998 | Omata |
| 5,769,846 A | 6/1998 | Edwards et al. |
| 5,792,045 A | 8/1998 | Adair |
| 5,797,903 A | 8/1998 | Swanson et al. |
| 5,823,947 A | 10/1998 | Yoon et al. |
| 5,827,268 A | 10/1998 | Laufer |
| 5,829,447 A | 11/1998 | Stevens et al. |
| 5,843,118 A | 12/1998 | Sepetka et al. |
| 5,848,969 A | 12/1998 | Panescu et al. |
| 5,860,974 A | 1/1999 | Abele |
| 5,860,991 A | 1/1999 | Klein et al. |
| 5,865,791 A | 2/1999 | Whayne et al. |
| 5,873,815 A | 2/1999 | Kerin et al. |
| 5,879,366 A | 3/1999 | Shaw et al. |
| 5,895,417 A | 4/1999 | Pomeranz et al. |
| 5,897,487 A | 4/1999 | Ouchi |
| 5,897,553 A | 4/1999 | Mulier et al. |
| 5,902,328 A | 5/1999 | LaFontaine et al. |
| 5,904,651 A | 5/1999 | Swanson et al. |
| 5,908,445 A | 6/1999 | Whayne et al. |
| 5,928,250 A | 7/1999 | Koike et al. |
| 5,929,901 A | 7/1999 | Adair et al. |
| 5,941,845 A | 8/1999 | Tu et al. |
| 5,944,690 A | 8/1999 | Falwell et al. |
| 5,964,755 A | 10/1999 | Edwards |
| 5,968,053 A | 10/1999 | Revelas |
| 5,971,983 A | 10/1999 | Lesh |
| 5,986,693 A | 11/1999 | Adair et al. |
| 5,997,571 A | 12/1999 | Farr et al. |
| 6,004,269 A | 12/1999 | Crowley et al. |
| 6,012,457 A | 1/2000 | Lesh |
| 6,024,740 A | 2/2000 | Lesh et al. |
| 6,027,501 A | 2/2000 | Goble et al. |
| 6,036,685 A | 3/2000 | Mueller |
| 6,043,839 A | 3/2000 | Adair et al. |
| 6,047,218 A | 4/2000 | Whayne et al. |
| 6,063,077 A | 5/2000 | Schaer |
| 6,063,081 A | 5/2000 | Mulier et al. |
| 6,068,653 A | 5/2000 | LaFontaine |
| 6,071,302 A | 6/2000 | Sinofsky et al. |
| 6,081,740 A | 6/2000 | Gombrich et al. |
| 6,086,528 A | 7/2000 | Adair |
| 6,086,534 A | 7/2000 | Kesten |
| 6,099,498 A | 8/2000 | Addis |
| 6,099,514 A | 8/2000 | Sharkey et al. |
| 6,102,905 A | 8/2000 | Baxter et al. |
| 6,112,123 A | 8/2000 | Kelleher et al. |
| 6,115,626 A | 9/2000 | Whayne et al. |
| 6,123,703 A | 9/2000 | Tu et al. |
| 6,123,718 A | 9/2000 | Tu et al. |

(56) References Cited

U.S. PATENT DOCUMENTS

| | | |
|---|---|---|
| 6,129,724 A | 10/2000 | Fleischman et al. |
| 6,139,508 A | 10/2000 | Simpson et al. |
| 6,142,993 A | 11/2000 | Whayne et al. |
| 6,152,144 A | 11/2000 | Lesh et al. |
| 6,156,350 A | 12/2000 | Constantz |
| 6,159,203 A | 12/2000 | Sinofsky |
| 6,161,543 A | 12/2000 | Cox et al. |
| 6,164,283 A | 12/2000 | Lesh |
| 6,167,297 A | 12/2000 | Benaron |
| 6,168,591 B1 | 1/2001 | Sinofsky |
| 6,168,594 B1 * | 1/2001 | LaFontaine et al. ........... 606/41 |
| 6,174,307 B1 | 1/2001 | Daniel et al. |
| 6,178,346 B1 | 1/2001 | Amundson et al. |
| 6,190,381 B1 | 2/2001 | Olsen et al. |
| 6,211,904 B1 | 4/2001 | Adair et al. |
| 6,224,553 B1 | 5/2001 | Nevo |
| 6,231,561 B1 | 5/2001 | Frazier et al. |
| 6,235,044 B1 | 5/2001 | Root et al. |
| 6,237,605 B1 | 5/2001 | Vaska et al. |
| 6,238,393 B1 | 5/2001 | Mulier et al. |
| 6,240,312 B1 | 5/2001 | Alfano et al. |
| 6,254,598 B1 | 7/2001 | Edwards et al. |
| 6,258,083 B1 | 7/2001 | Daniel et al. |
| 6,270,492 B1 | 8/2001 | Sinofsky |
| 6,275,255 B1 | 8/2001 | Adair et al. |
| 6,290,689 B1 | 9/2001 | Delaney et al. |
| 6,306,081 B1 | 10/2001 | Ishikawa et al. |
| 6,310,642 B1 | 10/2001 | Adair et al. |
| 6,311,692 B1 | 11/2001 | Vaska et al. |
| 6,314,962 B1 | 11/2001 | Vaska et al. |
| 6,314,963 B1 | 11/2001 | Vaska et al. |
| 6,315,777 B1 | 11/2001 | Comben |
| 6,315,778 B1 | 11/2001 | Gambale et al. |
| 6,322,536 B1 | 11/2001 | Rosengart et al. |
| 6,325,797 B1 | 12/2001 | Stewart et al. |
| 6,328,727 B1 | 12/2001 | Frazier et al. |
| 6,358,247 B1 | 3/2002 | Altman et al. |
| 6,358,248 B1 | 3/2002 | Mulier et al. |
| 6,375,654 B1 | 4/2002 | McIntyre |
| 6,379,345 B1 | 4/2002 | Constantz |
| 6,385,476 B1 | 5/2002 | Osadchy et al. |
| 6,387,043 B1 | 5/2002 | Yoon |
| 6,387,071 B1 | 5/2002 | Constantz |
| 6,394,096 B1 | 5/2002 | Constantz |
| 6,396,873 B1 | 5/2002 | Goldstein et al. |
| 6,398,780 B1 | 6/2002 | Farley et al. |
| 6,401,719 B1 | 6/2002 | Farley et al. |
| 6,409,722 B1 | 6/2002 | Hoey et al. |
| 6,416,511 B1 | 7/2002 | Lesh et al. |
| 6,419,669 B1 | 7/2002 | Frazier et al. |
| 6,423,051 B1 | 7/2002 | Kaplan et al. |
| 6,423,055 B1 | 7/2002 | Farr et al. |
| 6,423,058 B1 | 7/2002 | Edwards et al. |
| 6,428,536 B2 | 8/2002 | Panescu et al. |
| 6,440,119 B1 | 8/2002 | Nakada et al. |
| 6,458,151 B1 | 10/2002 | Saltiel |
| 6,464,697 B1 | 10/2002 | Edwards et al. |
| 6,474,340 B1 | 11/2002 | Vaska et al. |
| 6,475,223 B1 | 11/2002 | Werp et al. |
| 6,478,769 B1 | 11/2002 | Parker |
| 6,482,162 B1 | 11/2002 | Moore |
| 6,484,727 B1 | 11/2002 | Vaska et al. |
| 6,485,489 B2 | 11/2002 | Teirstein et al. |
| 6,488,671 B1 | 12/2002 | Constantz et al. |
| 6,494,902 B2 | 12/2002 | Hoey et al. |
| 6,497,705 B2 | 12/2002 | Comben |
| 6,500,174 B1 | 12/2002 | Maguire et al. |
| 6,502,576 B1 | 1/2003 | Lesh |
| 6,514,249 B1 | 2/2003 | Maguire et al. |
| 6,517,533 B1 | 2/2003 | Swaminathan |
| 6,527,979 B2 | 3/2003 | Constantz et al. |
| 6,532,380 B1 | 3/2003 | Close et al. |
| 6,533,767 B2 | 3/2003 | Johansson et al. |
| 6,537,272 B2 | 3/2003 | Christopherson et al. |
| 6,540,733 B2 | 4/2003 | Constantz et al. |
| 6,540,744 B2 | 4/2003 | Hassett et al. |
| 6,544,195 B2 | 4/2003 | Wilson et al. |
| 6,547,780 B1 | 4/2003 | Sinofsky |
| 6,558,375 B1 | 5/2003 | Sinofsky et al. |
| 6,562,020 B1 | 5/2003 | Constantz et al. |
| 6,572,609 B1 | 6/2003 | Farr et al. |
| 6,579,285 B2 | 6/2003 | Sinofsky |
| 6,585,732 B2 | 7/2003 | Mulier et al. |
| 6,587,709 B2 | 7/2003 | Solf et al. |
| 6,593,884 B1 | 7/2003 | Gilboa et al. |
| 6,605,055 B1 | 8/2003 | Sinofsky et al. |
| 6,613,062 B1 | 9/2003 | Leckrone et al. |
| 6,622,732 B2 | 9/2003 | Constantz |
| 6,626,855 B1 | 9/2003 | Weng et al. |
| 6,626,900 B1 | 9/2003 | Sinofsky et al. |
| 6,635,070 B2 | 10/2003 | Leeflang et al. |
| 6,645,202 B1 | 11/2003 | Pless et al. |
| 6,650,923 B1 | 11/2003 | Lesh et al. |
| 6,658,279 B2 | 12/2003 | Swanson et al. |
| 6,659,940 B2 | 12/2003 | Adler |
| 6,673,090 B2 | 1/2004 | Root et al. |
| 6,676,656 B2 | 1/2004 | Sinofsky |
| 6,679,836 B2 | 1/2004 | Couvillon, Jr. |
| 6,682,526 B1 | 1/2004 | Jones et al. |
| 6,689,128 B2 | 2/2004 | Sliwa, Jr. et al. |
| 6,692,430 B2 | 2/2004 | Adler |
| 6,701,581 B2 | 3/2004 | Senovich et al. |
| 6,701,931 B2 | 3/2004 | Sliwa, Jr. et al. |
| 6,702,780 B1 | 3/2004 | Gilboa et al. |
| 6,704,043 B2 | 3/2004 | Goldstein et al. |
| 6,706,039 B2 | 3/2004 | Mulier et al. |
| 6,712,798 B2 | 3/2004 | Constantz |
| 6,719,747 B2 | 4/2004 | Constantz et al. |
| 6,719,755 B2 | 4/2004 | Sliwa, Jr. et al. |
| 6,730,063 B2 | 5/2004 | Delaney et al. |
| 6,736,810 B2 | 5/2004 | Hoey et al. |
| 6,751,492 B2 | 6/2004 | Ben-Haim |
| 6,755,790 B2 | 6/2004 | Stewart et al. |
| 6,755,811 B1 | 6/2004 | Constantz |
| 6,764,487 B2 | 7/2004 | Mulier et al. |
| 6,771,996 B2 | 8/2004 | Bowe et al. |
| 6,773,402 B2 | 8/2004 | Govari et al. |
| 6,780,151 B2 | 8/2004 | Grabover et al. |
| 6,805,128 B1 | 10/2004 | Pless et al. |
| 6,805,129 B1 | 10/2004 | Pless et al. |
| 6,811,562 B1 | 11/2004 | Pless |
| 6,833,814 B2 | 12/2004 | Gilboa et al. |
| 6,840,923 B1 | 1/2005 | Lapcevic |
| 6,840,936 B2 | 1/2005 | Sliwa, Jr. et al. |
| 6,849,073 B2 | 2/2005 | Hoey et al. |
| 6,858,005 B2 | 2/2005 | Ohline et al. |
| 6,858,026 B2 | 2/2005 | Sliwa, Jr. et al. |
| 6,863,668 B2 | 3/2005 | Gillespie et al. |
| 6,866,651 B2 | 3/2005 | Constantz |
| 6,871,085 B2 * | 3/2005 | Sommer ....................... 600/374 |
| 6,887,237 B2 | 5/2005 | McGaffigan |
| 6,892,091 B1 | 5/2005 | Ben-Haim et al. |
| 6,896,690 B1 | 5/2005 | Lambrecht et al. |
| 6,899,672 B2 | 5/2005 | Chin et al. |
| 6,915,154 B1 | 7/2005 | Docherty et al. |
| 6,923,805 B1 | 8/2005 | LaFontaine et al. |
| 6,929,010 B2 | 8/2005 | Vaska et al. |
| 6,932,809 B2 | 8/2005 | Sinofsky |
| 6,939,348 B2 | 9/2005 | Malecki et al. |
| 6,942,657 B2 | 9/2005 | Sinofsky et al. |
| 6,949,095 B2 | 9/2005 | Vaska et al. |
| 6,953,457 B2 | 10/2005 | Farr et al. |
| 6,955,173 B2 | 10/2005 | Lesh |
| 6,962,589 B2 | 11/2005 | Mulier et al. |
| 6,971,394 B2 | 12/2005 | Sliwa, Jr. et al. |
| 6,974,464 B2 | 12/2005 | Quijano et al. |
| 6,979,290 B2 | 12/2005 | Mourlas et al. |
| 6,982,740 B2 | 1/2006 | Adair et al. |
| 6,984,232 B2 | 1/2006 | Vanney et al. |
| 6,994,094 B2 | 2/2006 | Schwartz |
| 7,019,610 B2 | 3/2006 | Creighton, IV et al. |
| 7,025,746 B2 | 4/2006 | Tal |
| 7,030,904 B2 | 4/2006 | Adair et al. |
| 7,041,098 B2 | 5/2006 | Farley et al. |

(56) References Cited

U.S. PATENT DOCUMENTS

| | | |
|---|---|---|
| 7,042,487 B2 | 5/2006 | Nakashima |
| 7,044,135 B2 | 5/2006 | Lesh |
| 7,052,493 B2 | 5/2006 | Vaska et al. |
| 7,090,683 B2 | 8/2006 | Brock et al. |
| 7,118,566 B2 | 10/2006 | Jahns |
| 7,156,845 B2 | 1/2007 | Mulier et al. |
| 7,163,534 B2 | 1/2007 | Brucker et al. |
| 7,166,537 B2 | 1/2007 | Jacobsen et al. |
| 7,169,144 B2 | 1/2007 | Hoey et al. |
| 7,186,214 B2 | 3/2007 | Ness |
| 7,207,984 B2 | 4/2007 | Farr et al. |
| 7,217,268 B2 | 5/2007 | Eggers et al. |
| 7,242,832 B2 | 7/2007 | Carlin et al. |
| 7,247,155 B2 | 7/2007 | Hoey et al. |
| 7,261,711 B2 | 8/2007 | Mulier et al. |
| 7,263,397 B2 | 8/2007 | Hauck et al. |
| 7,276,061 B2 | 10/2007 | Schaer et al. |
| 7,309,328 B2 | 12/2007 | Kaplan et al. |
| 7,435,248 B2 | 10/2008 | Taimisto et al. |
| 7,527,625 B2 | 5/2009 | Knight et al. |
| 7,534,204 B2 | 5/2009 | Starksen et al. |
| 7,569,052 B2 | 8/2009 | Phan et al. |
| 7,736,347 B2 | 6/2010 | Kaplan et al. |
| 7,758,499 B2 | 7/2010 | Adler |
| 7,860,555 B2 | 12/2010 | Saadat |
| 7,860,556 B2 | 12/2010 | Saadat |
| 2001/0005789 A1 | 6/2001 | Root et al. |
| 2001/0020126 A1 | 9/2001 | Swanson et al. |
| 2001/0031912 A1 | 10/2001 | Adler |
| 2001/0039416 A1 | 11/2001 | Moorman et al. |
| 2001/0047136 A1 | 11/2001 | Domanik et al. |
| 2001/0047184 A1 | 11/2001 | Connors |
| 2001/0052930 A1 | 12/2001 | Adair et al. |
| 2002/0004644 A1 | 1/2002 | Koblish |
| 2002/0026145 A1 | 2/2002 | Bagaoisan et al. |
| 2002/0054852 A1 | 5/2002 | Cate |
| 2002/0065455 A1 | 5/2002 | Ben-Haim et al. |
| 2002/0068853 A1 | 6/2002 | Adler |
| 2002/0080248 A1 | 6/2002 | Adair et al. |
| 2002/0087166 A1 | 7/2002 | Brock et al. |
| 2002/0087169 A1 | 7/2002 | Brock et al. |
| 2002/0091304 A1 | 7/2002 | Ogura et al. |
| 2002/0138088 A1 | 9/2002 | Nash et al. |
| 2002/0165598 A1 | 11/2002 | Wahr et al. |
| 2002/0169377 A1 | 11/2002 | Khairkhahan et al. |
| 2003/0036698 A1 | 2/2003 | Kohler et al. |
| 2003/0069593 A1 | 4/2003 | Tremulis et al. |
| 2003/0120142 A1 | 6/2003 | Dubuc et al. |
| 2003/0130572 A1 | 7/2003 | Phan et al. |
| 2003/0144657 A1 | 7/2003 | Bowe et al. |
| 2003/0171741 A1 | 9/2003 | Ziebol et al. |
| 2003/0181939 A1 | 9/2003 | Bonutti |
| 2003/0208222 A1 | 11/2003 | Zadno-Azizi |
| 2003/0212394 A1 | 11/2003 | Pearson et al. |
| 2003/0216720 A1 | 11/2003 | Sinofsky et al. |
| 2003/0220574 A1 | 11/2003 | Markus et al. |
| 2003/0222325 A1 | 12/2003 | Jacobsen et al. |
| 2004/0006333 A1 | 1/2004 | Arnold et al. |
| 2004/0049211 A1 | 3/2004 | Tremulis et al. |
| 2004/0054335 A1 | 3/2004 | Lesh et al. |
| 2004/0054389 A1 | 3/2004 | Osypka |
| 2004/0082833 A1 | 4/2004 | Adler |
| 2004/0097788 A1 | 5/2004 | Mourlas et al. |
| 2004/0117032 A1 | 6/2004 | Roth |
| 2004/0133113 A1 | 7/2004 | Krishnan |
| 2004/0138707 A1 | 7/2004 | Greenhalgh |
| 2004/0147806 A1 | 7/2004 | Adler |
| 2004/0147911 A1 | 7/2004 | Sinofsky |
| 2004/0147912 A1 | 7/2004 | Sinofsky |
| 2004/0147913 A1 | 7/2004 | Sinofsky |
| 2004/0158143 A1 | 8/2004 | Flaherty et al. |
| 2004/0158289 A1 | 8/2004 | Girouard et al. |
| 2004/0167503 A1 | 8/2004 | Sinofsky |
| 2004/0181237 A1 | 9/2004 | Forde et al. |
| 2004/0199052 A1 | 10/2004 | Banik et al. |
| 2004/0210239 A1 | 10/2004 | Nash et al. |
| 2004/0215183 A1 | 10/2004 | Hoey et al. |
| 2004/0220471 A1 | 11/2004 | Schwartz |
| 2004/0230131 A1 | 11/2004 | Kassab et al. |
| 2004/0248837 A1 | 12/2004 | Raz et al. |
| 2004/0254523 A1 | 12/2004 | Fitzgerald et al. |
| 2004/0260182 A1 | 12/2004 | Zuluaga et al. |
| 2005/0014995 A1 | 1/2005 | Amundson et al. |
| 2005/0015048 A1 | 1/2005 | Chiu et al. |
| 2005/0020914 A1 | 1/2005 | Amundson et al. |
| 2005/0027163 A1 | 2/2005 | Chin et al. |
| 2005/0038419 A9 | 2/2005 | Arnold et al. |
| 2005/0059862 A1 | 3/2005 | Phan |
| 2005/0059954 A1 | 3/2005 | Constantz |
| 2005/0059965 A1 | 3/2005 | Eberl et al. |
| 2005/0065504 A1 | 3/2005 | Melsky et al. |
| 2005/0090818 A1 | 4/2005 | Pike, Jr. et al. |
| 2005/0096643 A1 | 5/2005 | Brucker et al. |
| 2005/0101984 A1 | 5/2005 | Chanduszko et al. |
| 2005/0107736 A1 | 5/2005 | Landman et al. |
| 2005/0119523 A1 | 6/2005 | Starksen et al. |
| 2005/0124969 A1 | 6/2005 | Fitzgerald et al. |
| 2005/0131401 A1 | 6/2005 | Malecki et al. |
| 2005/0154252 A1 | 7/2005 | Sharkey et al. |
| 2005/0158899 A1 | 7/2005 | Jacobsen et al. |
| 2005/0159702 A1 | 7/2005 | Sekiguchi et al. |
| 2005/0165279 A1 | 7/2005 | Adler et al. |
| 2005/0165391 A1 | 7/2005 | Maguire et al. |
| 2005/0165466 A1 | 7/2005 | Morris et al. |
| 2005/0182465 A1 | 8/2005 | Ness |
| 2005/0197530 A1 | 9/2005 | Wallace et al. |
| 2005/0197623 A1 | 9/2005 | Leeflang et al. |
| 2005/0215895 A1 | 9/2005 | Popp et al. |
| 2005/0222557 A1 | 10/2005 | Baxter et al. |
| 2005/0222558 A1 | 10/2005 | Baxter et al. |
| 2005/0228452 A1 | 10/2005 | Mourlas et al. |
| 2005/0234436 A1 | 10/2005 | Baxter et al. |
| 2005/0234437 A1 | 10/2005 | Baxter et al. |
| 2005/0267328 A1 | 12/2005 | Blumzvig et al. |
| 2005/0267452 A1 | 12/2005 | Farr et al. |
| 2006/0009715 A1 | 1/2006 | Khairkhahan et al. |
| 2006/0009737 A1 | 1/2006 | Whiting et al. |
| 2006/0015096 A1 | 1/2006 | Hauck et al. |
| 2006/0022234 A1 | 2/2006 | Adair et al. |
| 2006/0025651 A1 | 2/2006 | Adler et al. |
| 2006/0025787 A1 | 2/2006 | Morales et al. |
| 2006/0030844 A1 | 2/2006 | Knight et al. |
| 2006/0069303 A1 | 3/2006 | Couvillon et al. |
| 2006/0074398 A1 | 4/2006 | Whiting et al. |
| 2006/0084839 A1 | 4/2006 | Mourlas et al. |
| 2006/0084945 A1 | 4/2006 | Moll et al. |
| 2006/0089637 A1 | 4/2006 | Werneth et al. |
| 2006/0111614 A1 | 5/2006 | Saadat et al. |
| 2006/0122587 A1 | 6/2006 | Sharareh |
| 2006/0146172 A1 | 7/2006 | Jacobsen et al. |
| 2006/0149331 A1 | 7/2006 | Mann et al. |
| 2006/0155242 A1 | 7/2006 | Constantz |
| 2006/0161133 A1 | 7/2006 | Laird et al. |
| 2006/0167439 A1 | 7/2006 | Kalser et al. |
| 2006/0183992 A1 | 8/2006 | Kawashima |
| 2006/0184048 A1* | 8/2006 | Saadat .................. 600/478 |
| 2006/0217755 A1 | 9/2006 | Eversull et al. |
| 2006/0224167 A1 | 10/2006 | Weisenburgh et al. |
| 2006/0253113 A1 | 11/2006 | Arnold et al. |
| 2006/0271032 A1 | 11/2006 | Chin et al. |
| 2007/0005019 A1 | 1/2007 | Okishige |
| 2007/0015964 A1 | 1/2007 | Eversull et al. |
| 2007/0016130 A1 | 1/2007 | Leeflang et al. |
| 2007/0043338 A1 | 2/2007 | Moll et al. |
| 2007/0043413 A1 | 2/2007 | Eversull et al. |
| 2007/0049923 A1 | 3/2007 | Jahns |
| 2007/0078451 A1 | 4/2007 | Arnold et al. |
| 2007/0083187 A1 | 4/2007 | Eversull et al. |
| 2007/0083217 A1 | 4/2007 | Eversull et al. |
| 2007/0093808 A1 | 4/2007 | Mulier et al. |
| 2007/0100241 A1 | 5/2007 | Adler |
| 2007/0100324 A1 | 5/2007 | Tempel et al. |
| 2007/0106146 A1 | 5/2007 | Altmann et al. |
| 2007/0106214 A1 | 5/2007 | Gray et al. |

(56) References Cited

U.S. PATENT DOCUMENTS

| | | | |
|---|---|---|---|
| 2007/0106287 A1 | 5/2007 | O'Sullivan | |
| 2007/0135826 A1 | 6/2007 | Zaver et al. | |
| 2007/0167801 A1 | 7/2007 | Webler et al. | |
| 2007/0265609 A1 | 11/2007 | Thapliyal et al. | |
| 2007/0265610 A1 | 11/2007 | Thapliyal et al. | |
| 2007/0270686 A1 | 11/2007 | Ritter et al. | |
| 2007/0287886 A1* | 12/2007 | Saadat | 600/115 |
| 2007/0293724 A1 | 12/2007 | Saadat et al. | |
| 2008/0009747 A1 | 1/2008 | Saadat et al. | |
| 2008/0009859 A1 | 1/2008 | Auth et al. | |
| 2008/0015445 A1 | 1/2008 | Saadat et al. | |
| 2008/0015563 A1 | 1/2008 | Hoey et al. | |
| 2008/0015569 A1 | 1/2008 | Saadat et al. | |
| 2008/0027464 A1 | 1/2008 | Moll et al. | |
| 2008/0033290 A1 | 2/2008 | Saadat et al. | |
| 2008/0057106 A1 | 3/2008 | Erickson et al. | |
| 2008/0058590 A1 | 3/2008 | Saadat et al. | |
| 2008/0058836 A1 | 3/2008 | Moll et al. | |
| 2008/0097476 A1 | 4/2008 | Peh et al. | |
| 2008/0183081 A1 | 7/2008 | Lys et al. | |
| 2008/0188759 A1* | 8/2008 | Saadat et al. | 600/478 |
| 2008/0214889 A1 | 9/2008 | Saadat et al. | |
| 2008/0228032 A1 | 9/2008 | Starksen et al. | |
| 2008/0275300 A1* | 11/2008 | Rothe | A61B 1/0008 600/129 |
| 2008/0281293 A1 | 11/2008 | Peh et al. | |
| 2008/0287790 A1 | 11/2008 | Li | |
| 2008/0287805 A1 | 11/2008 | Li | |
| 2009/0030412 A1* | 1/2009 | Willis et al. | 606/41 |
| 2009/0054803 A1 | 2/2009 | Saadat et al. | |
| 2009/0062790 A1 | 3/2009 | Malchano et al. | |
| 2009/0076489 A1 | 3/2009 | Welches et al. | |
| 2009/0076498 A1 | 3/2009 | Saadat et al. | |
| 2009/0125022 A1* | 5/2009 | Saadat et al. | 606/41 |
| 2009/0143640 A1 | 6/2009 | Saadat et al. | |
| 2009/0264727 A1 | 10/2009 | Markowitz et al. | |
| 2009/0267773 A1 | 10/2009 | Markowitz et al. | |
| 2010/0004506 A1 | 1/2010 | Saadat | |
| 2010/0004661 A1 | 1/2010 | Verin et al. | |
| 2011/0060227 A1 | 3/2011 | Saadat | |
| 2011/0060298 A1 | 3/2011 | Saadat | |
| 2011/0144576 A1 | 6/2011 | Rothe et al. | |

FOREIGN PATENT DOCUMENTS

| | | |
|---|---|---|
| EP | 0301288 A1 | 2/1999 |
| JP | 59093413 A | 5/1984 |
| JP | 59-181315 | 10/1984 |
| JP | 01-221133 | 9/1989 |
| JP | 03-284265 | 12/1991 |
| JP | 05-103746 | 4/1993 |
| JP | 09-051897 | 2/1997 |
| JP | 11-299725 | 11/1999 |
| JP | 2001-258822 | 9/2001 |
| WO | WO 92/21292 | 12/1992 |
| WO | WO 94/07413 | 4/1994 |
| WO | WO 95/03843 | 2/1995 |
| WO | WO 98/18388 | 5/1998 |
| WO | WO 03/039350 | 5/2003 |
| WO | WO 03/053491 | 7/2003 |
| WO | WO 03/101287 | 12/2003 |
| WO | WO 2004/043272 | 5/2004 |
| WO | WO 2004/080508 | 9/2004 |
| WO | WO 2005/070330 | 8/2005 |
| WO | WO 2005/077435 | 8/2005 |
| WO | WO 2005/081202 | 9/2005 |
| WO | WO 2006/017517 | 2/2006 |
| WO | WO 2006/024015 | 3/2006 |
| WO | WO 2006/083794 | 8/2006 |
| WO | WO 2006/091597 | 8/2006 |
| WO | WO 2006/126979 | 11/2006 |
| WO | WO 2007/067323 | 6/2007 |
| WO | WO 2007/079268 | 7/2007 |
| WO | WO 2007/133845 | 11/2007 |
| WO | WO 2007/134258 | 11/2007 |
| WO | WO 2008/015625 | 2/2008 |
| WO | WO 2008/021994 | 2/2008 |
| WO | WO 2008/021997 | 2/2008 |
| WO | WO 2008/021998 | 2/2008 |
| WO | WO 2008/024261 | 2/2008 |
| WO | WO 2008/079828 | 7/2008 |
| WO | WO 2009/112262 | 9/2009 |

OTHER PUBLICATIONS

Avitall, "Right-Sided Driven Atrial Fibrillation in a Sterile Pericarditis Dog Model", PACE, vol. 17, p. 774, 1994.

Avitall, "Vagally Mediated Atrial Fibrillation in a Dog Model can be Ablated by Placing Linear Radiofrequency Lesions at the Junction of the Right Atrial Appendage and the Superior Vena Cava", PACE, vol. 18, p. 857, 1995.

Baker, "Nonpharmacologic Approaches to the Treatment of Atrial Fibrillation and Atrial Flutter", J. Cardiovasc. Electrophysiol., vol. 6, pp. 972-978, 1995.

Bhakta, "Principles of Electroanatomic Mapping", Indian Pacing & Electrophysiol J., vol. 8, No. 1, pp. 32-50, 2008.

Bidoggia, "Transseptal Left Heart Catheterization: Usefulness of the Intracavitary Electrocardiogram in the Localization of the Fossa Ovalis", Cathet Cardiovasc Diagn., vol. 24, No. 3, pp. 221-225, 1991.

Bredikis, "Surgery of Tachyarrhythmia: Intracardiac Closed Heart Cryoablation", PACE, vol. 13, pp. 1980-1984, 1990.

Cox, "Cardiac Surgery for Arrhythmias", J. Cardiovasc. Electrophysiol., vol. 15, pp. 250-262, 2004.

Cox, "Five-Year Experience With the Maze Procedure for Atrial Fibrillation", The Annals Thoracic Surgery, vol. 56, pp. 814-824, 1993.

Cox, "Modification of the Maze Procedure for Atrial Flutter and Atrial Fibrillation", The Journal of Thoracic and Cardiovascular Surgery, vol. 110, pp. 473-484, 1995.

Cox, "The Status of Surgery for Cardiac Arrhythmias", Circulation, vol. 71, pp. 413-417, 1985.

Cox, "The Surgical Treatment of Atrial Fibrillation", The Journal of Thoracic and Cardiovascular Surgery, vol. 101, pp. 584-592, 1991.

Elvan, Replication of the "Maze" Procedure by Radiofrequency Catheter Ablation Reduces the Ability to Induce Atrial Fibrillation, PACE, vol. 17, p. 774, 1994.

Elvan, Radiofrequency Catheter Ablation (RFCA) of the Atria Effectively Abolishes Pacing Induced Chronic Atrial Fibrillation, PACE, vol. 18, p. 856, 1995.

Elvan, Radiofrequency Catheter Ablation of the Atria Reduces Inducibility and Duration of Atrial Fibrillation in Dogs, Circulation, vol. 91, pp. 2235-2244, 1995.

European Patent Application No. 06734083.6 filed Jan. 30, 2006 in the name of Saadat et al., Examination Communication dated May 18, 2010.

European Patent Application No. 06734083.6 filed Jan. 30, 2006 in the name of Saadat et al., extended European Search Report dated Jul. 1, 2009.

European Patent Application No. 06734083.6 filed Jan. 30, 2006 in the name of Saadat et al., office action dated Oct. 23, 2009.

European Patent Application No. 07841754.0 filed Aug. 31, 2007 in the name of Saadat et al., Supplemental European Search Report dated Jun. 30, 2010.

European Patent Application No. 08746822.9 filed Apr. 24, 2008 in the name of Rothe et al., European Search Report dated Mar. 29, 2010.

European Patent Application No. 08746822.9 filed Apr. 24, 2008 in the name of Rothe et al., Office Action dated Jul. 13, 2010.

Fieguth, Inhibition of Atrial Fibrillation by Pulmonary Vein Isolation and Auricular Resection—Experimental Study in a Sheep Model, European J. Cardiothorac. Surg., vol. 11, pp. 714-721, 1997.

Hoey, Intramural Ablation Using Radiofrequency Energy Via Screw-Tip Catheter and Saline Electrode, PACE, vol. 18, p. 487, 1995.

(56) References Cited

OTHER PUBLICATIONS

Huang, Increase in the Lesion Size and Decrease in the Impedance Rise with a Saline Infusion Electrode Catheter for Radiofrequency, Circulation, vol. 80, No. 4, pp. II-324, 1989.
Moser, Angioscopic Visualization of Pulmonary Emboli, CHEST, vol. 77, No. 2, pp. 198-201, 1980.
Nakamura, Percutaneous Intracardiac Surgery With Cardioscopic Guidance, SPIE, vol. 1652, pp. 214-216, 1992.
Pappone, Circumferential Radiofrequency Ablation of Pulmonary Vein Ostia, Circulation, vol. 102, pp. 2619-2628, 2000.
Sethi, Transseptal Catheterization for the Electrophysiologist: Modification with a "View", J. Interv. Card. Electrophysiol., vol. 5, pp. 97-99, 2001, Kluwer Academic Publishers, Netherlands.
Thiagalingam, Cooled Needle Catheter Ablation Creates Deeper and Wider Lesions than Irrigated Tip Catheter Ablation, J. Cardiovasc. Electrophysiol., vol. 16, pp. 1-8, 2005.
U.S. Appl. No. 11/259,498, filed Oct. 25, 2005 in the name of Saadat et al., Non-final Office Action dated Feb. 25, 2010.
U.S. Appl. No. 11/560,742, filed Nov. 16, 2006 in the name of Saadat, Non-final Office Action dated Jun. 10, 2010.
U.S. Appl. No. 11/687,597, filed Mar. 16, 2007 in the name of Saadat et al., Non-final Office Action dated Jul. 21, 2010.
U.S. Appl. No. 11/828,267, filed Jul. 25, 2007 in the name of Saadat et al., Non-final Office Action dated Jan. 14, 2010.
U.S. Appl. No. 12/117,655, filed May 8, 2008 in the name of Peh et al., Final Office Action dated Mar. 1, 2010.
U.S. Appl. No. 12/117,655, filed May 8, 2008 in the name of Saadat et al., Non-final Office Action dated Jun. 8, 2009.
U.S. Appl. No. 61/286,283, filed Dec. 14, 2009 in the name of Rothe et al.
U.S. Appl. No. 61/297,462, filed Jan. 22, 2010 in the name of Rothe et al.
Uchida, Developmental History of Cardioscopes, Coronary Angioscopy, pp. 187-197, 2001, Futura Publishing Co., Armonk, NY.
Willkampf, Radiofrequency Ablation with a Cooled Porous Electrode Catheter, JACC, vol. 11, No. 2, p. 17A, 1988.
U.S. Appl. No. 11/775,771, filed Jul. 10, 2007 in the name of Saadat et al., Non-final Office Action dated Aug. 27, 2010.
U.S. Appl. No. 11/828,267, filed Jul. 25, 2007 in the name of Saadat et al., final Office Action dated Sep. 16, 2010.
U.S. Appl. No. 11/259,498, filed Oct. 25, 2005 in the name of Saadat, Notice of Allowance dated Nov. 15, 2010.
U.S. Appl. No. 11/560,742, filed Nov. 16, 2006 in the name of Saadat, Notice of Allowance dated Nov. 15, 2010.
U.S. Appl. No. 12/464,800, filed May 12, 2009 in the name of Peh et al., non-final Office Action dated Nov. 24, 2010.
U.S. Appl. No. 11/848,429, filed Aug. 31, 2007 in the name of Peh et al., non-final Office Action dated Nov. 24, 2010.
European Patent Application No. 06734083.6 filed Jan. 30, 2006 in the name of Voyage Medical, Inc., Office Action dated Nov. 12, 2010.
European Patent Application No. 07812146.4 filed Jun. 14, 2007 in the name of Voyage Medical, Inc., European Search Report dated Nov. 18, 2010.
European Patent Application No. 07799466.3 filed Jul. 10, 2007 in the name of Voyage Medical, Inc., European Search Report dated Nov. 18, 2010.
U.S. Appl. No. 12/117,655, filed May 8, 2008 in the name of Peh et al., non-final Office Action dated Dec. 16, 2010.
U.S. Appl. No. 12/026,455, filed Feb. 5, 2008 in the name of Saadat et al., non-final Office Action dated Dec. 27, 2010.
U.S. Appl. No. 12/947,198, filed Nov. 16, 2010 in the name of Saadat, non-final Office Action dated Feb. 18, 2011.
U.S. Appl. No. 11/560,732, filed Nov. 16, 2006 in the name of Saadat, Notice of Allowance dated Feb. 3, 2011.
U.S. Appl. No. 12/947,246, filed Nov. 16, 2006 in the name of Saadat, non-final Office Action dated Feb. 18, 2011.
U.S. Appl. No. 11/687,597, filed Mar. 16, 2007 in the name of Saadat, Notice of Allowance dated Feb. 24, 2011.
U.S. Appl. No. 11/560,732, filed Mar. 16, 2007 in the name of Saadat, Notice of Allowance dated Feb. 24, 2011.
U.S. Appl. No. 11/848,207, filed Aug. 30, 2007 in the name of Saadat et al., non-final Office Action dated Feb. 25, 2011.
Japanese Patent Application No. 2007-554156 filed Jan. 30, 2006 in the name of Voyage Medical, Inc., Office Action dated Feb. 15, 2011.
European Patent Application No. 07758716.0 filed Mar. 16, 2007 in the name of Voyage Medical, Inc., Supplemental European Search Report dated Feb. 28, 2011.
U.S. Appl. No. 11/848,202, filed Aug. 30, 2007 in the name of Saadat et al., non-final Office Action dated Mar. 11, 2011.
U.S. Appl. No. 11/763,399, filed Jun. 14, 2007 in the name of Saadat et al., non-final Office Action dated Apr. 11, 2011.
U.S. Appl. No. 12/499,011, filed Jul. 7, 2009 in the name of Rothe et al., non-final Office Action dated Apr. 12, 2011.
U.S. Appl. No. 12/367,019, filed Feb. 6, 2009 in the name of Miller et al., non-final Office Action dated Apr. 22, 2011.
U.S. Appl. No. 11/959,158, filed Dec. 18, 2007 in the name of Saadat et al., non-final Office Action dated Apr. 25, 2011.
U.S. Appl. No. 11/848,532, filed Aug. 31, 2007 in the name of Saadat et al., non-final Office Action dated Apr. 26, 2011.
U.S. Appl. No. 11/828,281, filed Jul. 25, 2007 in the name of Peh et al., non-final Office Action dated Apr. 27, 2011.
U.S. Appl. No. 11/961,950, filed Dec. 20, 2007 in the name of Saadat et al., non-final Office Action dated May 9, 2011.
U.S. Appl. No. 11/961,995, filed Dec. 20, 2007 in the name of Saadat et al., non-final Office Action dated May 9, 2011.
U.S. Appl. No. 11/962,029, filed Dec. 20, 2007 in the name of Saadat et al., non-final Office Action dated May 9, 2011.
U.S. Appl. No. 11/828,267, filed Jul. 25, 2007 in the name of Saadat et al., non-final Office Action dated May 11, 2011.
Japanese Patent Application No. 2009-500630 filed Mar. 16, 2007 in the name of Voyage Medical, Inc., Office Action dated Apr. 27, 2011.
U.S. Appl. No. 11/775,771, filed Jul. 10, 2007 in the name of Saadat et al., final Office Action dated May 12, 2011.
U.S. Appl. No. 11/877,386, filed Oct. 23, 2007 in the name of Saadat et al., non-final Office Action dated May 20, 2011.
U.S. Appl. No. 11/775,819, filed Jul. 10, 2007 in the name of Saadat et al., non-final Office Action dated May 20, 2011.
U.S. Appl. No. 11/775,837, filed Jul. 10, 2007 in the name of Saadat et al., non-final Office Action dated May 23, 2011.
U.S. Appl. No. 12/117,655, filed May 8, 2008 in the name of Peh et al., final Office Action dated Jun. 2, 2011.
U.S. Appl. No. 12/323,281, filed Nov. 25, 2008 in the name of Saadat et al., non-final Office Action dated Jun. 7, 2011.
Japanese Patent Application No. 2007-554156 filed Jan. 30, 2006 in the name of Voyage Medical, Inc., Notice of Allowance dated Jun. 13, 2011.
Voyage Medical, Inc., Notice of Allowance dated Jun. 13, 2011.

\* cited by examiner

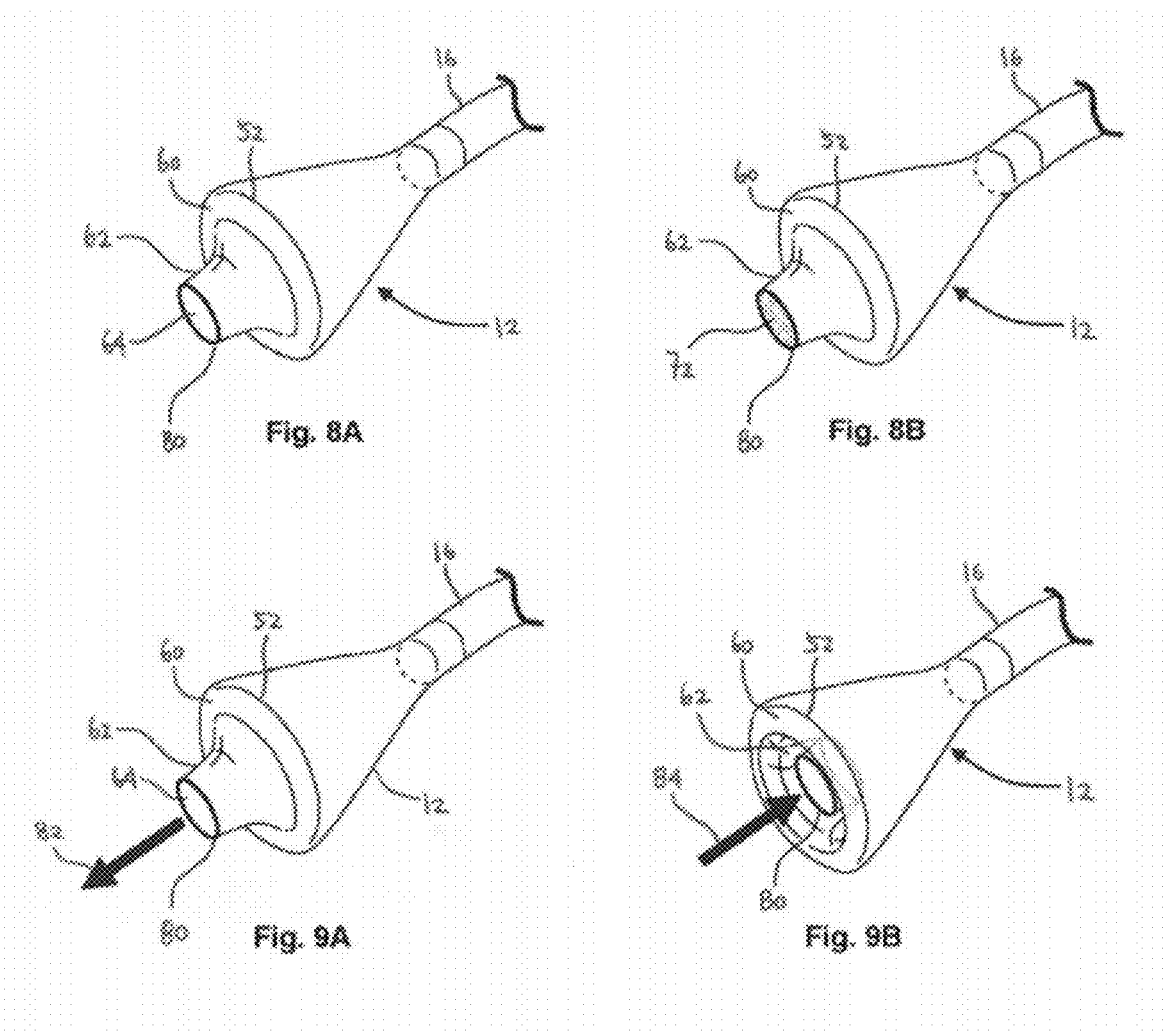

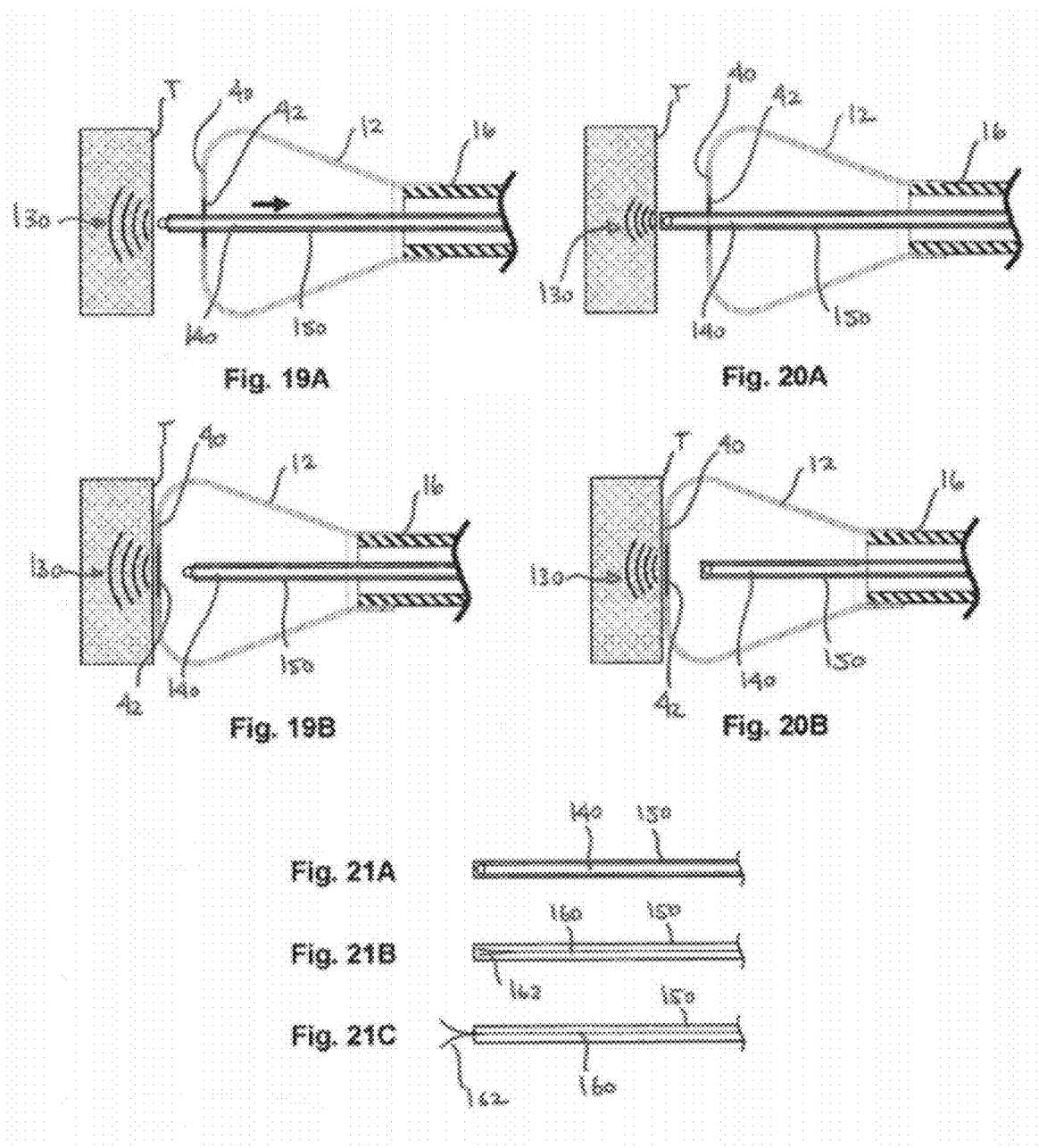

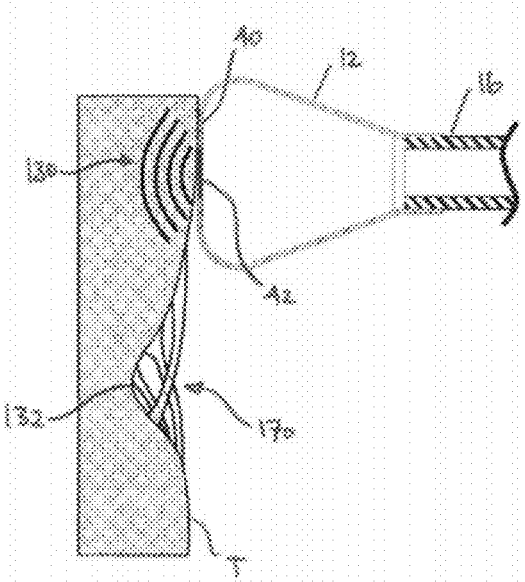
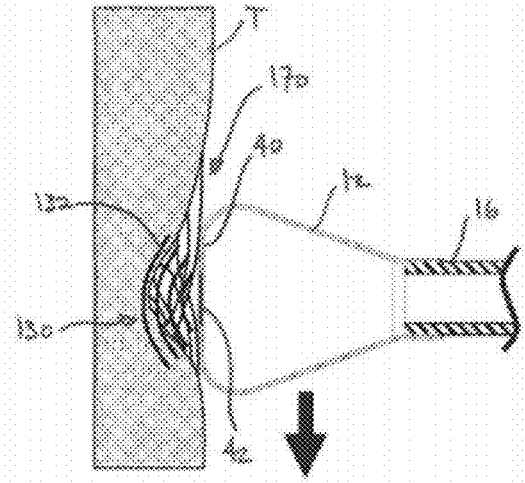
Fig. 22A
Fig. 22B
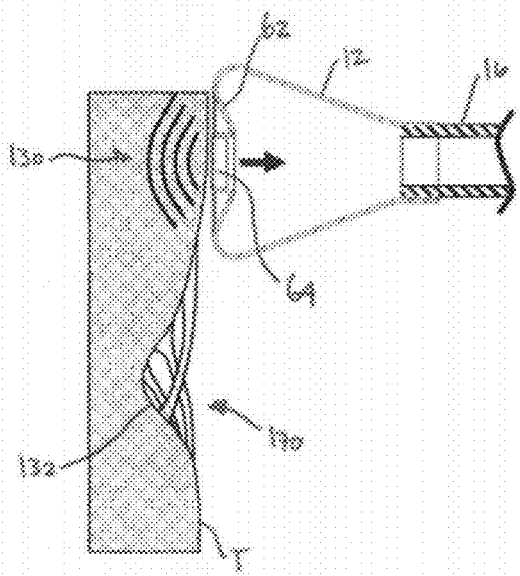
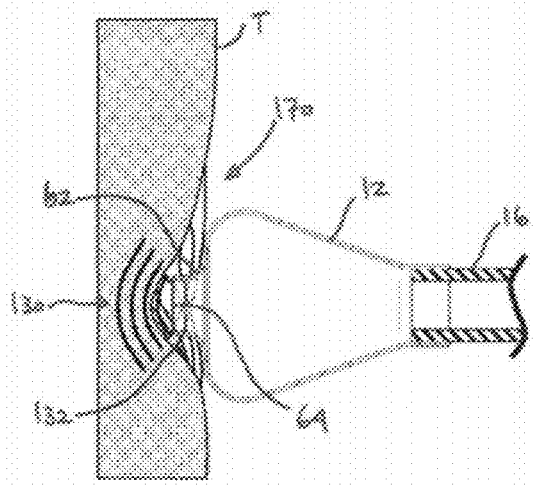
Fig. 23A
Fig. 23B

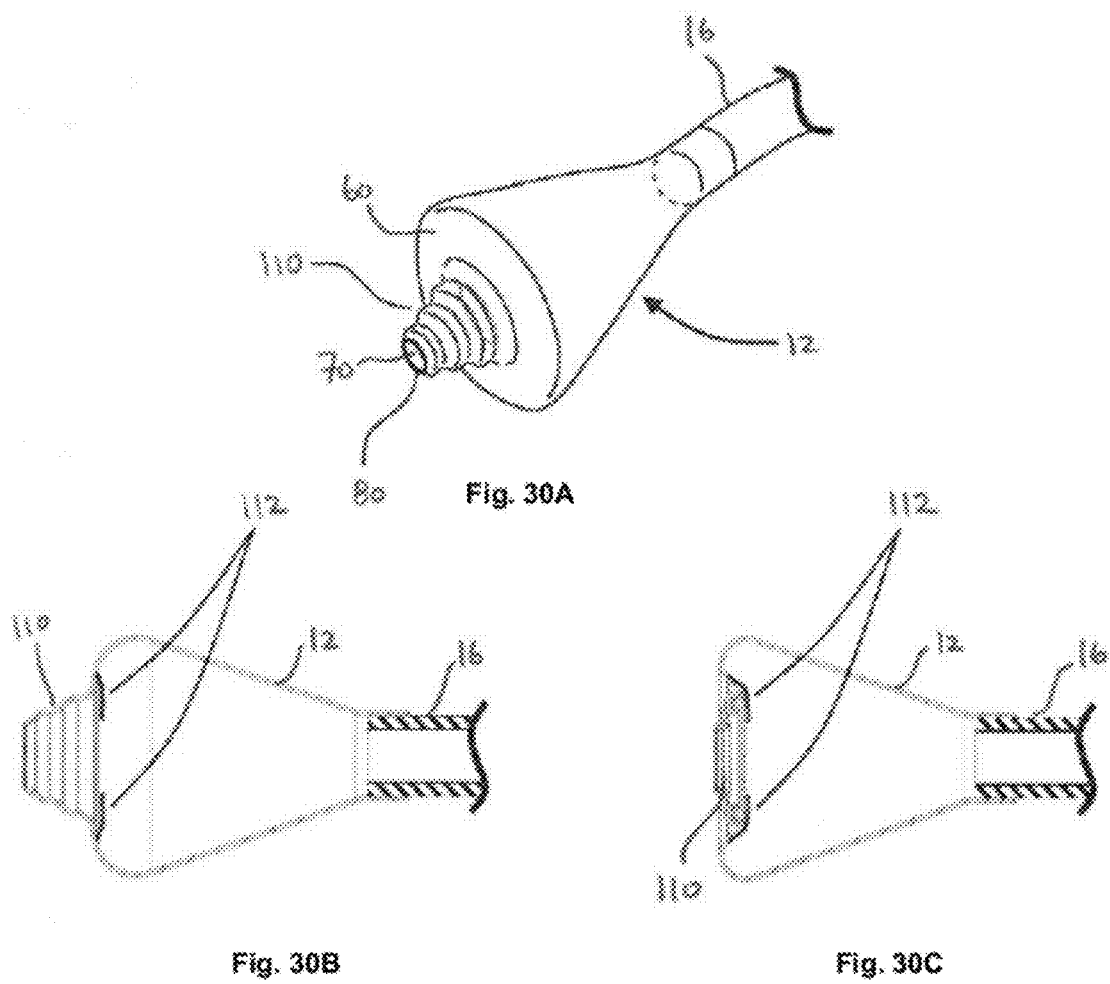

APPARATUS AND METHODS FOR ABLATION EFFICACY

CROSS-REFERENCE TO RELATED APPLICATIONS

This application claims the benefit of priority to U.S. Prov. App. 61/321,471 filed Apr. 6, 2010, which is incorporated herein by reference in its entirety.

FIELD OF THE INVENTION

The present invention relates generally to catheter control systems and methods for stabilizing images of moving tissue regions such as a heart which are captured when intravascularly accessing and/or treating regions of the body.

BACKGROUND OF THE INVENTION

Conventional devices for accessing and visualizing interior regions of a body lumen are known. For example, various catheter devices are typically advanced within a patient's body, e.g., intravascularly, and advanced into a desirable position within the body. Other conventional methods have utilized catheters or probes having position sensors deployed within the body lumen, such as the interior of a cardiac chamber. These types of positional sensors are typically used to determine the movement of a cardiac tissue surface or the electrical activity within the cardiac tissue. When a sufficient number of points have been sampled by the sensors, a "map" of the cardiac tissue may be generated.

Another conventional device utilizes an inflatable balloon which is typically introduced intravascularly in a deflated state and then inflated against the tissue region to be examined. Imaging is typically accomplished by an optical fiber or other apparatus such as electronic chips for viewing the tissue through the membrane(s) of the inflated balloon. Moreover, the balloon must generally be inflated for imaging. Other conventional balloons utilize a cavity or depression formed at a distal end of the inflated balloon. This cavity or depression is pressed against the tissue to be examined and is flushed with a clear fluid to provide a clear pathway through the blood.

However, many of the conventional catheter imaging systems lack the capability to provide therapeutic treatments or are difficult to manipulate in providing effective therapies. For instance, the treatment in a patient's heart for atrial fibrillation is generally made difficult by a number of factors, such as visualization of the target tissue, access to the target tissue, and instrument articulation and management, amongst others.

Conventional catheter techniques and devices, for example such as those described in U.S. Pat. Nos. 5,895, 417; 5,941,845; and 6,129,724, used on the epicardial surface of the heart may be difficult in assuring a transmural lesion or complete blockage of electrical signals. In addition, current devices may have difficulty dealing with varying thickness of tissue through which a transmural lesion is desired.

Conventional accompanying imaging devices, such as fluoroscopy, are unable to detect perpendicular electrode orientation, catheter movement during the cardiac cycle, and image catheter position throughout lesion formation. The absence of real-time visualization also poses the risk of incorrect placement and ablation of structures such as sinus node tissue which can lead to fatal consequences.

Moreover, because of the uneven anatomy of tissue surfaces, imaging devices which can accommodate various anatomies as well as effectively deliver energy to these tissue regions with uneven surfaces are desirable.

SUMMARY OF THE INVENTION

A tissue-imaging and manipulation apparatus described herein which may be used for ablation by passing energy such as an electric current through the clearing fluid such that the energy passes directly to the tissue region being imaged and the electrical energy is conducted through the fluid without the need for a separate ablation probe or instrument to ablate the tissue being viewed. Details of such visual electrode ablation systems are described in further detail in U.S. patent application Ser. No. 12/118,439 filed May 9, 2008 (U.S. Pat. Pub. 2009/0030412), which is incorporated herein by reference in its entirety. Mechanisms for channeling the energy to the deeper regions of tissue or instruments which may deploy the effective position of the hood aperture beyond the surface of the hood may be utilized so that the energy can be delivered to the target tissue despite small or large irregularities in the target tissue surface and/or changes in the relative distances between the hood and the target tissue.

One variation is a hood assembly which defines an aperture but has a distal membrane which is relatively more rounded or, extended beyond the circumferential atraumatic contact lip or edge defined by the hood. This variation of the rounded distal membrane may be used to treat tissue surfaces with some depressions or pockets or invaginations. Alternatively, an elongated tubular or conduit features that extend from the distal membrane of the hood may also be designed, configured, or shaped such that they enter, nest, or, locate within the areas of the tissue surface with invaginations due to the mechanical resilience and/or shape of the feature. Another variation may include a hood assembly having an elongated feature and an additional fluid permeable feature, such as a screen, mesh, grating, or porous membrane through which fluid can exchange yet with limited transport in order to better limit blood from entering the hood.

The elongated feature may also contain a stiffening element around the aperture where the stiffening member may minimize distortion at the aperture that could potentially affect the opening area so as to prevent the energy delivered per unit time from altering during delivery. The stiffening element may comprise any number of shapes (e.g., partial or complete hoop, ring, band, etc.) and may further comprise any number of biocompatible materials (shape memory metals, polymers, any combination of materials, etc.) that provides a substantially stiffer component than the hood material member and can be utilized to predictably support the shape of the hood aperture and thereby maintain an accurate energy density during energy delivery. Prior to deployment, the stiffening member may be configured into a collapsed low-profile shape for delivery, e.g., through a sheath, with the collapsed hood but once deployed, the stiffening member can regain its pre-deformed shape.

Additionally and/or optionally, the elongated tubular/conduit feature can be collapsed or retracted (within the hood open area) when visualizing along tissue surfaces or treating the tissue, if so desired, such that the hood face can maintain close contact relative to the tissue. Deployment and/or retraction of the elongated feature may be accomplished by a number of different mechanisms. For example, the elongated feature may be preferentially configured due to the nature of the material or to the molding of the feature to become biased in one or both configurations. In this example, if elongated feature is retracted within the expanded hood, the introduction of the clearing fluid within the hood may push or urge the elongated feature to deploy. Additionally, retraction of the elongated feature may be accomplished by depressing the feature against a tissue surface such that the feature is biased to invaginate or deflect inwardly with respect to the rest of the hood.

Another variation may incorporate a fluid permeable feature such that when the interior of the hood is pressurized to create an internal positive pressure, the elongated feature may be urged to extend or deploy from the hood. Similarly, the hood interior may be de-pressurized to create an internal negative and/or reduced pressure that effectively retracts the elongated feature proximally into the open area of the hood. The elongated feature may be configured to deploy and/or retract at predetermined pressures.

Another variation of the hood may incorporate a relatively rigid internal support member attached to the stiffening member which may be pushed or pulled axially through the catheter to impart a force, to the stiffening member. In use, the internal support member may be selectively pushed relative to the catheter and hood to deploy the elongated feature. Similarly, the support member may be selectively pulled to retract the elongated feature.

In any of the variations shown and described herein, the permeable feature may be optionally incorporated over the aperture with or without the elongated features to provide additional rigidity to the hood shape while being partially pressurized with fluid for flushing/irrigating. This added rigidity may minimize distortions and deformations of the hood aperture and therefore facilitate an even energy density distribution during ablation.

In yet another variation, alternatively and/or additionally to the elongated feature, an electrode tipped shaft or catheter may be advanced or retracted through the catheter and hood open area to deliver energy either through the hood aperture or distal to the aperture. In yet another variation, the electrode having a slidable sheath can be advanced through the hood open area where a position of the sheath can be independently controlled relative to the electrode. By adjusting the position of sheath relative to the electrode location, the amount of exposed surface area of the electrode can be controlled to adjust the output energy density given a certain power setting to adjust the lesion formation characteristics.

Yet another variation of the hood may further incorporate an optional porous or fluid dispersing feature over the aperture. In this example, the porous or fluid dispersing feature may generally comprise a cap-like or domed structure which curves distally beyond the hood face in an arcuate manner. The fluid dispersing feature may define one or more (e.g., a plurality) of openings over the feature which allow for the free passage of the clearing fluid through the feature in a dispersed manner much like a shower head. The feature may be energized or charged via one or more connections, e.g., through support struts, to provide for the application of energy through the clearing fluid as the fluid is dispersed through the feature. Accordingly, the feature may be comprised of a metallic or electrically conductive material. Alternatively, the clearing fluid may be energized via an electrode within the hood interior and then pass through the dispersing feature to the underlying tissue. In other variations, the fluid dispersing feature may instead be configured as a tubular or cylindrical structure which covers the aperture and further extends distally from the hood.

BRIEF DESCRIPTION OF THE DRAWINGS

FIGS. 8A and 8B show perspective views of hood variations having an elongated feature with an optional stiffening element and permeable feature.

FIGS. 9A and 9B show perspective views of another variation of an elongated feature in deployed and retracted states.

FIGS. 19A and 19B show cross-sectional side views of an electrode instrument advanced distally of the aperture and positioned within the open area of the hood.

FIGS. 20A and 20B show cross-sectional side views of an electrode instrument with the sheath advanced distally of the aperture and positioned within the open area of the hood.

FIGS. 21A to 21C show variations of electrode instruments.

FIGS. 22A and 22B show cross-sectional side views of a hood delivering energy through the hood aperture within a region of trabeculae which inhibits the hood from advancing further and further inhibits the energy from effectively reaching the targeted tissue.

FIGS. 23A and 23B show cross-sectional side views of a hood having the elongated feature extended within the trabeculae to more effectively deliver energy to the underlying tissue region.

FIGS. 30A to 30C show perspective and cross-sectional side views of a hood having an internal member or ridge which limits the excursion of the corrugated surface as it is compressed within the hood open area.

DETAILED DESCRIPTION OF THE INVENTION

A tissue-imaging and manipulation apparatus described herein is able to provide real-time images in vivo of tissue regions within a body lumen such as a heart, which is filled with blood flowing dynamically therethrough and is also able to provide intravascular tools and instruments for performing various procedures upon the imaged tissue regions. Such an apparatus may be utilized for many procedures, e.g., facilitating transseptal access to the left atrium, cannulating the coronary sinus, diagnosis of valve regurgitation/stenosis, valvuloplasty, atrial appendage closure, arrhythmogenic focus ablation, among other procedures. Although intravascular applications are described, other extravascular approaches or applications may be utilized with the devices and methods herein.

Figure 1A:
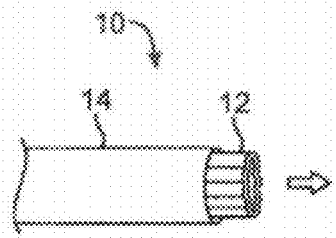
FIG. 1A shows a side view of one variation of a tissue imaging apparatus during deployment from a sheath or delivery catheter.
Figure 1B:
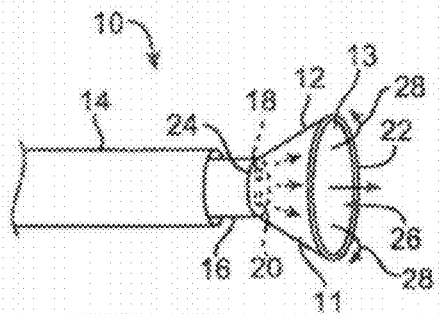
FIG. 1B shows the deployed tissue imaging apparatus of FIG. 1A having an optionally expandable hood or sheath attached to an imaging and/or diagnostic catheter.
Figure 1C:
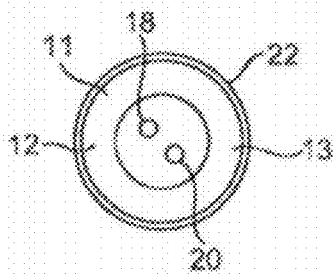
FIG. 1C shows an end view of a deployed imaging apparatus.

One variation of a tissue access and imaging apparatus is shown in the detail perspective views of FIGS. 1A to 1C. As shown in FIG. 1A, tissue imaging and manipulation assembly 10 may be delivered intravascularly through the patient's body in a low-profile configuration via a delivery catheter or sheath 14. In the case of treating tissue, it is generally desirable to enter or access the left atrium while minimizing trauma to the patient. To non-operatively effect such access, one conventional approach involves puncturing the intra-atrial septum from the right atrial chamber to the left atrial chamber in a procedure commonly called a transseptal procedure or septostomy. For procedures such as percutaneous valve repair and replacement, transseptal access to the left atrial chamber of the heart may allow for larger devices to be introduced into the venous system than can generally be introduced percutaneously into the arterial system.

When the imaging and manipulation assembly 10 is ready to be utilized for imaging tissue, imaging hood 12 may be advanced relative to catheter 14 and deployed from a distal opening of catheter 14, as shown by the arrow. Upon deployment, imaging hood 12 may be unconstrained to expand or open into a deployed imaging configuration, as shown in FIG. 1B. Imaging hood 12 may be fabricated from a variety of pliable or conformable biocompatible material including but not limited to, e.g., polymeric, plastic, or woven materials. One example of a woven material is Kevlar® (E. I. du Pont de Nemours, Wilmington, Del.), which is an aramid and which can be made into thin, e.g., less than 0.001 in., materials which maintain enough integrity for such applications described herein. Moreover, the imaging hood 12 may be fabricated from a translucent or opaque material and in a variety of different colors to optimize or attenuate any reflected lighting from surrounding fluids or structures, i.e., anatomical or mechanical structures or instruments. In either case, imaging hood 12 may be fabricated into a uniform structure or a scaffold-supported structure, in which case a scaffold made of a shape memory alloy, such as Nitinol, or a spring steel, or plastic, etc., may be fabricated and covered with the polymeric, plastic, or woven material. Hence, imaging hood 12 may comprise any of a wide variety of barriers or membrane structures, as may generally be used to localize displacement of blood or the like from a selected volume of a body lumen or heart chamber. In exemplary embodiments, a volume within an inner surface 13 of imaging hood 12 will be significantly less than a volume of the hood 12 between inner surface 13 and outer surface 11. Additionally, as the hood 12 functions as a barrier or membrane between the fluid in the environment surrounding the hood and the interior of the hood, the hood may comprise a non-inflatable membrane which may be configured to be self-expanding or optionally actuated.

Imaging hood 12 may be attached at interface 24 to a deployment catheter 16 which may be translated independently of deployment catheter or sheath 14. Attachment of interface 24 may be accomplished through any number of conventional methods. Deployment catheter 16 may define a fluid delivery lumen 18 as well as an imaging lumen 20 within which an optical imaging fiber or assembly may be disposed for imaging tissue. When deployed, imaging hood 12 may expand into any number of shapes, e.g., cylindrical, conical as shown, semi-spherical, etc., provided that an open area or field 26 is defined by imaging hood 12. The open area 26 is the area within which the tissue region of interest may be imaged. Imaging hood 12 may also define an atraumatic contact lip or edge 22 for placement or abutment against the tissue region of interest. Moreover, the diameter of imaging hood 12 at its maximum fully deployed diameter, e.g., at contact lip or edge 22, is typically greater relative to a diameter, of the deployment catheter 16 (although a diameter of contact lip or edge 22 may be made to have a smaller or equal diameter of deployment catheter 16). For instance, the contact edge diameter may range anywhere from 1 to 5 times (or even greater, as practicable) a diameter of deployment catheter 16. FIG. 1C shows an end view of the imaging hood 12 in its deployed configuration. Also shown are the contact lip or edge 22 and fluid delivery lumen 18 and imaging lumen 20.

Figure 2A:
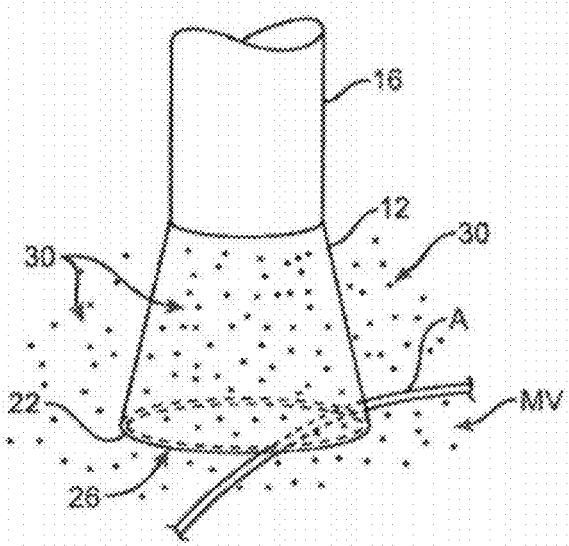
FIGS. 2A and 2B show one example of a deployed tissue imager positioned against or adjacent to the tissue to be imaged and a flow of fluid, such as saline, displacing blood from within the expandable hood.
Figure 2B:
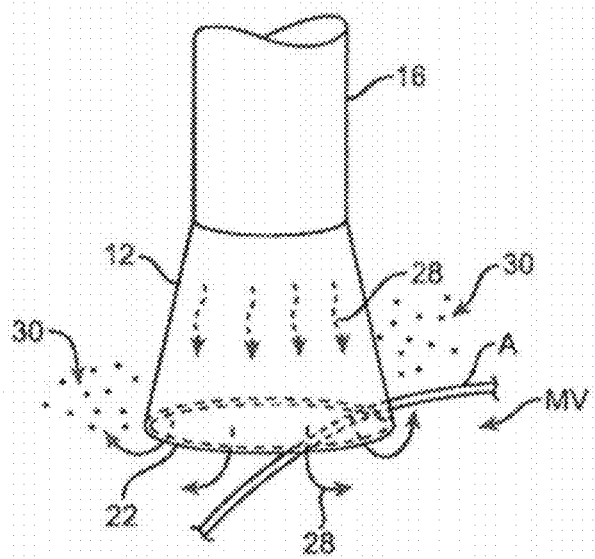

As seen in the example of FIGS. 2A and 2B, deployment catheter 16 may be manipulated to position deployed imaging hood 12 against or near the underlying tissue region of interest to be imaged, in this example a portion of annulus A of mitral valve MV within the left atrial chamber. As the surrounding blood 30 flows around imaging hood 12 and within open area 26 defined within imaging hood 12, as seen in FIG. 2A, the underlying annulus A is obstructed by the opaque blood 30 and is difficult to view through the imaging lumen 20. The translucent fluid 28, such as saline, may then be pumped through fluid delivery lumen 18, intermittently or continuously, until the blood 30 is at least partially, and preferably completely, displaced from within open area 26 by fluid 28, as shown in FIG. 2B.

Although contact edge 22 need not directly contact the underlying tissue, it is at least preferably brought into close proximity to the tissue such that the flow of clear fluid 28 from open area 26 may be maintained to inhibit significant backflow of blood 30 back into open area 26. Contact edge 22 may also be made of a soft elastomeric material such as certain soft grades of silicone or polyurethane, as typically known, to help contact edge 22 conform to an uneven or rough underlying anatomical tissue surface. Once the blood 30 has been displaced from imaging hood 12, an image may then be viewed of the underlying tissue through the clear fluid 30. This image may then be recorded or available for real-time viewing for performing a therapeutic procedure. The positive flow of fluid 28 may be maintained continuously to provide for clear viewing of the underlying tissue. Alternatively, the fluid 28 may be pumped temporarily or sporadically only until a clear view of the tissue is available to be imaged and recorded, at which point the fluid flow 28 may cease and blood 30 may be allowed to seep or flow back into imaging hood 12. This process may be repeated a number of times at the same tissue region or at multiple tissue regions.

Figure 3A:
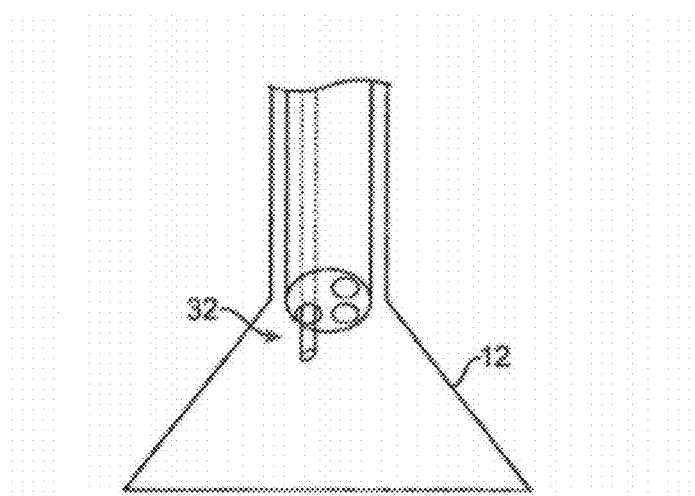
FIGS. 3A and 3B show examples of various visualization imagers which may be utilized within or along the imaging hood.
Figure 3B:
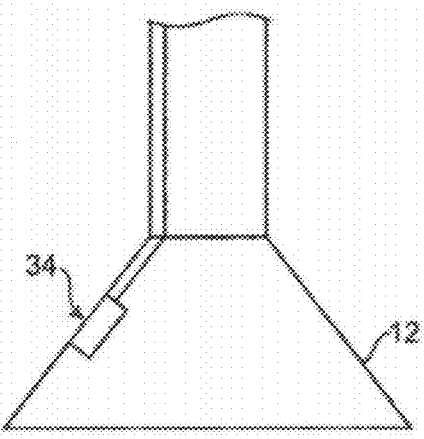

FIG. 3A shows a partial cross-sectional view of an example where one or more optical fiber bundles 32 may be positioned, within the catheter and within imaging hood 12 to provide direct in-line imaging of the open area within hood 12. FIG. 3B shows another example where an imaging element 34 (e.g., CCD or CMOS electronic imager) may be placed along an interior surface of imaging hood 12 to provide imaging of the open area such that the imaging element 34 is off-axis relative to a longitudinal axis of the hood 12, as described in further detail below. The off-axis position of element 34 may provide for direct visualization and uninhibited access by instruments from the catheter to the underlying tissue during treatment.

Figure 4A:
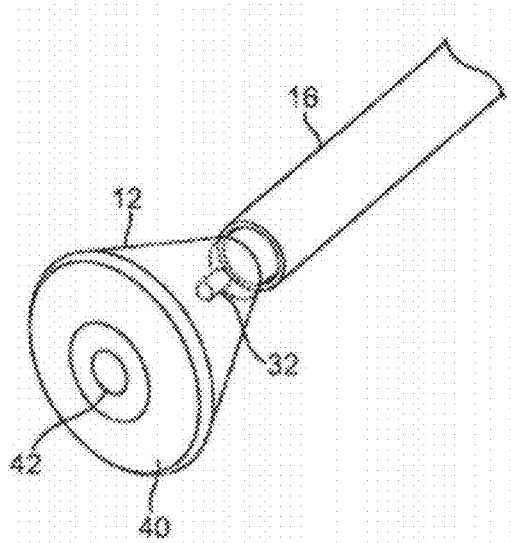
FIGS. 4A and 4B show perspective and end views, respectively, of an imaging hood having at least one layer of a transparent elastomeric membrane over the distal opening of the hood.
Figure 4B:
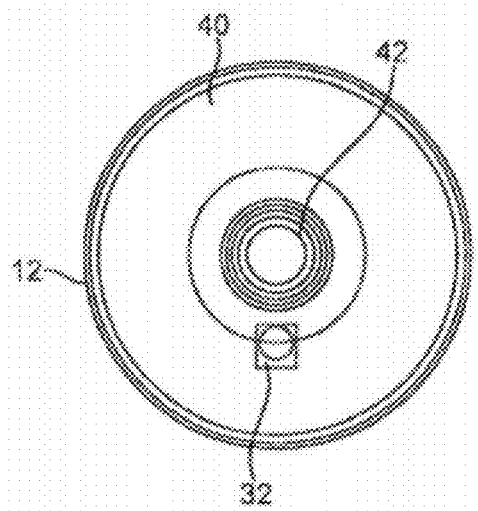

In utilizing the imaging hood 12 in any one of the procedures described herein, the hood 12 may have an open field which is uncovered and clear to provide direct tissue contact between the hood interior and the underlying tissue to effect any number of treatments upon the tissue, as described above. Yet in additional variations, imaging hood 12 may utilize other configurations. An additional variation of the imaging hood 12 is shown in the perspective and end views, respectively, of FIGS. 4A and 4B, where imaging hood 12 includes at least one layer of a transparent elastomeric membrane 40 over the distal opening of hood 12. An aperture 42 having a diameter which is less than a diameter of the outer lip of imaging hood 12 may be defined over the center of membrane 40 where a longitudinal axis of the hood intersects the membrane such that the interior of hood 12 remains open and in fluid communication with the environment external to hood 12. Furthermore, aperture 42 may be sized, e.g., between 1 to 2 mm or more in diameter and membrane 40 can be made from any number of transparent elastomers such as silicone, polyurethane, latex, etc. such that contacted tissue may also be visualized through membrane 40 as well as through aperture 42.

Aperture 42 may function generally as a restricting passageway to reduce the rate of fluid out-flow from the hood 12 when the interior of the hood 12 is infused with the clear fluid through which underlying tissue regions may be visualized. Aside from restricting out-flow of clear fluid from within hood 12, aperture 42 may also restrict external surrounding fluids from entering hood 12 too rapidly. The reduction in the rate of fluid out-flow from the hood and blood in-flow into the hood may improve visualization conditions as hood 12 may be more readily filled with transparent fluid rather than being filled by opaque blood which may obstruct direct visualization by the visualization instruments.

Moreover, aperture 42 may be aligned with catheter 16 such that any instruments (e.g., piercing instruments, guidewires, tissue engagers, etc.) that are advanced into the hood interior may directly access the underlying tissue uninhibited or unrestricted for treatment through aperture 42. In other variations wherein aperture 42 may not be aligned with catheter 16, instruments passed through catheter 16 may still access the underlying tissue by simply piercing through membrane 40.

Figure 5A:
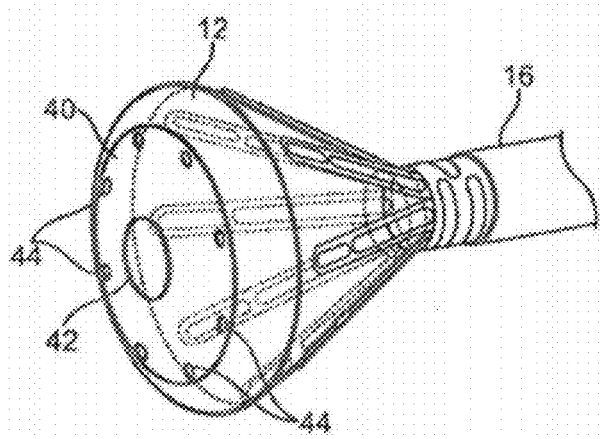
FIGS. 5A and 5B show perspective and end views, respectively, of an imaging hood which includes a membrane with an aperture defined therethrough and a plurality of additional openings defined over the membrane surrounding the aperture.
Figure 5B:
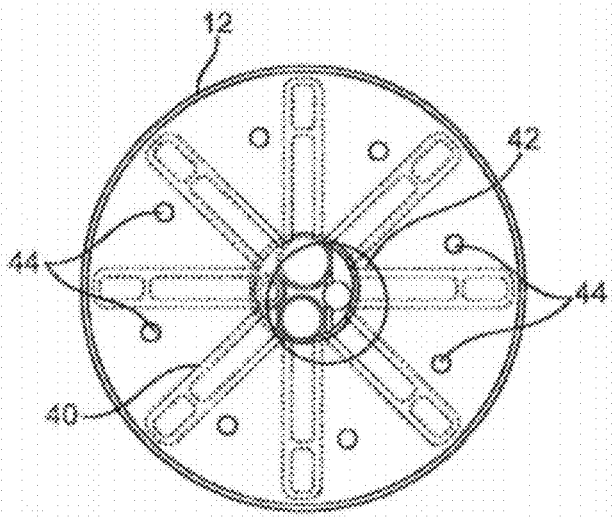

In an additional variation, FIGS. 5A and 5B show perspective and end views, respectively, of imaging hood 12 which includes membrane 40 with aperture 42 defined therethrough, as described above. This variation includes a plurality of additional openings 44 defined over membrane 40 surrounding aperture 42. Additional openings 44 may be uniformly sized, e.g., each less than 1 mm in diameter, to allow for the out-flow of the translucent fluid therethrough when in contact against the tissue surface. Moreover, although openings 44 are illustrated as uniform in size, the openings may be varied in size and their placement may also be non-uniform or random over membrane 40 rather than uniformly positioned about aperture 42 in FIG. 5B. Furthermore, there are eight openings 44 shown in the figures although fewer than eight or more than eight openings 44 may also be utilized over membrane 40.

In utilizing the devices and methods above, various procedures may be accomplished. One example of such a procedure is crossing a tissue region such as in a transseptal procedure where a septal wall is pierced and traversed, e.g., crossing from a right atrial chamber to a left atrial chamber in a heart of a subject. Generally, in piercing and traversing a septal wall, the visualization and treatment devices described herein may be utilized for visualizing the tissue region to be pierced as well as monitoring the piercing and access through the tissue. Details of transseptal visualization catheters and methods for transseptal access which may be utilized with the apparatus and methods described herein are described in U.S. patent application Ser. No. 11/763,399 filed Jun. 14, 2007 (U.S. Pat. Pub. 2007/0293724 A1), which is incorporated herein by reference in its entirety. Additionally, details of tissue visualization and manipulation catheter which may be utilized with apparatus and methods described herein are described in U.S. patent application Ser. No. 11/259,498 filed Oct. 25, 2005 (U.S. Pat. Pub. 2006/0184048 A1), which is incorporated herein by reference in its entirety.

Moreover, any of the variations described herein may be used for ablation by passing energy such as an electric current through the clearing fluid such that the energy passes directly to the tissue region being imaged and the electrical energy is conducted through the fluid without the need for a separate ablation probe or instrument to ablate the tissue being viewed. Details of such visual electrode ablation systems are described in further detail in U.S. patent application Ser. No. 12/118,439 filed May 9, 2008 (U.S. Pat. Pub. 2009/0030412), which is incorporated herein by reference in its entirety.

When ablating tissue within the chambers of the heart, target tissue regions that are generally inaccessible or deep (e.g., distal) to the hood 12 or which are obstructed by trabeculae or other tissue structures may receive less controlled power (or focused energy density) than tissue directly adjacent to the hood aperture. Mechanisms for channeling the energy to the deeper regions of tissue or instruments which may deploy the effective position of the hood aperture beyond the surface of the hood may be utilized so that the energy can be delivered to the target tissue despite small or large irregularities in the target tissue surface and/or changes in the relative distances between the hood and the target tissue. Furthermore, mechanisms and techniques for excising, cutting and/or disrupting tissue that covers or obstructs the deeper tissue regions in order to allow the hood to be delivered even further distal are also disclosed.

Figure 6A:
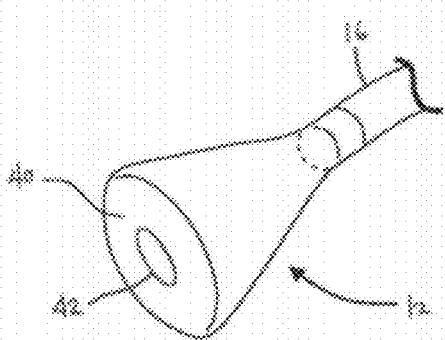
FIG. 6A shows a perspective view of a hood having a flattened distal membrane that can be used to treat most relatively flat tissue surfaces.
Figure 6B:
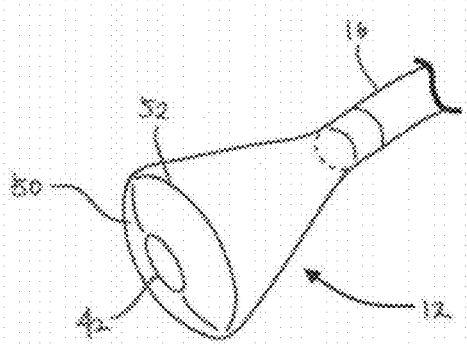
FIG. 6B shows a perspective view of a hood having a rounded distal membrane.

FIG. 6A shows a perspective view of hood 12 having distal membrane 40 which defines the aperture 42 for comparison. The hood 12 may be used to treat most tissue surfaces which are relatively flattened or unobstructed. FIG. 6B shows another example in the perspective view of hood 12 having a distal membrane 50 which defines aperture 42 but also has a distal membrane 50 which is relatively more rounded or extended beyond the circumferential atraumatic contact lip or edge 52 defined by the hood 12. This variation of the rounded distal membrane 50 may be used to treat tissue surfaces with some depressions or pockets or invaginations.

The hood 12 generally enables direct visualization of tissue in a blood-filled environment by maintaining a positive flow of the clearing fluid, such as saline or other suitable liquid, that may intermittently or continuously purge blood from the open area of the hood 12 through the aperture 42 at the distal membrane 40 thereby creating an optically clear visual pathway that extends to the tissue surface intimate to the front of the hood 12. Direct apposition of the tissue to the hood distal membrane 40 may ensure good image quality and also minimize the intrusion of blood into the hood open area that could potentially degrade the clarity of the optical path. Additionally, the position of the hood 12 may be typically maintained in an orientation normal to the tissue surface relative to the catheter longitudinal axis in order to provide the most even, uniform, or least obstructed visualization field and also to prevent uneven fluid leakage from the hood aperture 42 that could also allow blood to enter the hood open area.

As described in further detail in U.S. patent application Ser. No. 12/118,439 (which has been incorporated by reference hereinabove), hood 12 can be utilized for direct ablation of tissue by energizing the fluid retained temporarily within the open area of the hood by one or more electrodes mounted within or along the hood to create a virtual electrode. The electrolytic clearing fluid is used as the energy conductor in order to ablate the tissue adjacent or in proximity to the aperture while also allowing direct visualization of the lesion formation. Direct visualization of the underlying tissue also ensures that the proper position, location, and proximity to structures or other lesions is well determined and/or identified prior to beginning, during, or after the ablation procedure.

There are several factors that can affect the efficiency and efficacy of the ablation process while utilizing such a hood structure. For example, the area of the hood aperture can be relatively constant so that the energy density is maintained during the ablation sequence/procedure. Area changes of the aperture may affect or alter the energy density and the effective power delivered which may change the lesion formation characteristics in the tissue. Additionally, the position of the one or more electrodes within the hood can impact the energy density given a specific output power and therefore can affect lesion formation. Also the distance of the hood aperture from the surface of the tissue can have an impact as well particularly if there is a sufficiently large gap, due to the potential fall-off of energy density as the current leaks out to the large blood and fluid volume surrounding the hood and ultimately directs or focuses less of the energy to the target tissue. Therefore, maintaining intimate contact with the tissue and preventing distortion of the opening are desirable parameters to control in order to ensure efficient and consistent lesion formation.

Furthermore, the ability of the hood 12 to accommodate irregularities in the tissue surface (e.g., recesses, voids, invaginations, etc.) and having a hood aperture maintained in relatively close proximity to the tissue surface despite changes in orientation of the overall hood structure relative to the tissue surface are also desirable in controlling the energy delivery even despite different and varying tissue surface geometries, conditions, anatomies, anomalies, and pathologies. By having a substantially curved or rounded distal membrane 50, as shown in FIG. 6B, can help the hood 12 to engage with varying tissue surfaces.

Figure 7A:
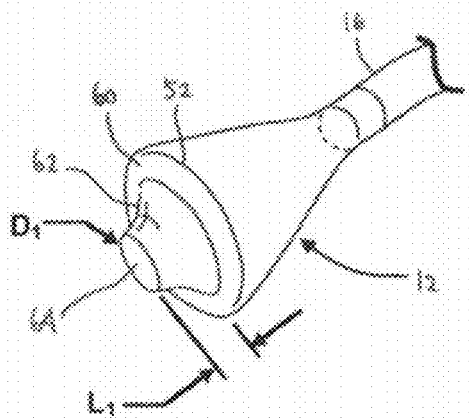
FIGS. 7A to 7D show perspective views of various hoods having an elongated feature that extends distally from the front surface of the hood.

Alternatively, elongated tubular or conduit features that extend from the distal membrane of the hood may also be designed, configured, or shaped such that they enter, nest, or locate within the areas of the tissue surface with invaginations due to the mechanical resilience and/or shape of the feature. One example is shown where the aperture of the hood may be extended even farther distally from the contact lip or edge 52 to reach deeper tissue regions for more direct or intimate energy delivery. FIG. 7A shows an example in the perspective view of hood 12 having an elongated feature 62 that projects distally from the surface 60 of the hood 12 at a length L1, e.g., x1-x2 cm, and may narrow from an initial wider diameter down to a relatively smaller diameter D1, e.g., y1-y2 cm, which defines the aperture 64.

Figure 7C:
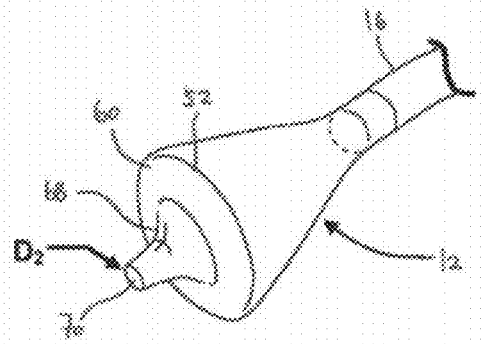
Figure 7B:
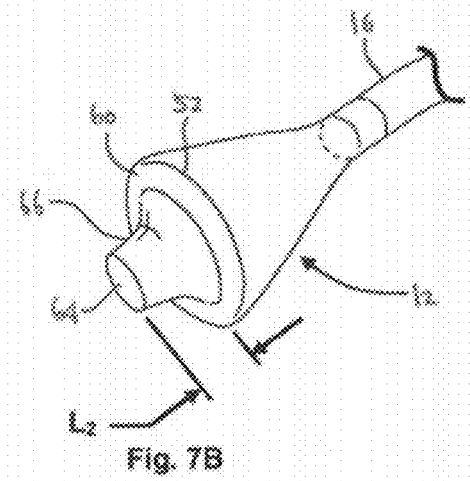
Figure 7D:
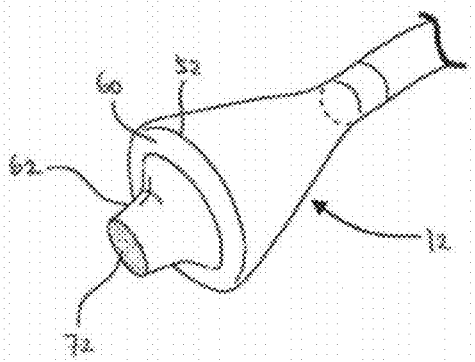

FIG. 7B shows a perspective view of another example where the elongated feature 66 extends even further with at a length of L2, e.g., z1-z2 cm, which is relatively longer than the elongated feature 62 of FIG. 7A to treat even deeper tissue invaginations or regions. In this example, the elongated feature 66 may narrow from an initial diameter down to a narrower diameter D1 similarly to the diameter shown in FIG. 7A. Another variation is shown in the perspective view of FIG. 7C which shows elongated feature 68 which may narrow from an initial diameter to a relatively smaller diameter D2, e.g., a1-a2 cm, which defines the aperture 70 in order to enter tissue regions with more closely spaced features or structures. FIG. 7D shows another example in the perspective view of hood 12 with an elongated feature 62 which may narrow in diameter from an initial wider diameter to the smaller diameter D1 with an additional fluid permeable feature 72, such as a screen, mesh, grating, or porous membrane through which fluid can exchange yet with limited transport in order to better limit blood from entering the hood 12.

FIG. 8A shows another variation in the perspective view of hood 12 with elongated feature 62 which also contains a stiffening element 80 around the aperture 64 where the stiffening member 80 may minimize distortion at the aperture that could potentially affect the opening area so as to prevent the energy delivered per unit time from altering during delivery. Stiffening element 80 may comprise any number of shapes (e.g., partial or complete hoop, ring, band, etc.) and may further comprise any number of biocompatible materials (shape memory metals, polymers, any combination of materials, etc.) that provides a substantially stiffer component than the hood material member and can be utilized to predictably support the shape of the hood aperture and thereby maintain an accurate energy density during energy delivery. Prior to deployment, stiffening member 80 may be configured into a collapsed low-profile shape for delivery, e.g., through a sheath, with the collapsed hood 12 but once deployed, the stiffening member 80 can regain its pre-deformed shape. FIG. 8B shows a perspective view of the hood 12 of FIG. 8A but with an additional fluid permeable feature 72 optionally incorporated over the aperture.

Additionally and/or optionally, the elongated tubular/conduit feature can be collapsed or retracted (within the hood open area) when visualizing along tissue surfaces or treating the tissue, if so desired, such that the hood face can maintain close contact relative to the tissue. As illustrated in the perspective views of FIGS. 9A and 9B, the elongated feature 62 may be optionally deployed 82 from a retracted position within the opened hood 12 into the deployed profile shown in FIG. 9A. The elongated feature 62 may be optionally retracted 84 proximally into the hood open area, as shown in FIG. 9B, for facilitating contact between the distal membrane 60 and the tissue surface or for removal of the hood assembly. Deployment 82 and/or retraction 84 of the elongated feature 62 may be accomplished by a number of different mechanisms. For example, the elongated feature 62 may be preferentially configured due to the nature of the material or to the molding of the feature to become biased in one or both configurations. In this example, if elongated feature 62 is retracted within the expanded hood 12, the introduction of the clearing fluid within the hood 12 may push or urge the elongated feature 62 to deploy. Additionally, retraction of the elongated feature 62 may be accomplished by depressing the feature 62 against a tissue surface such that the feature 62 is biased to invaginate or deflect inwardly with respect to the rest of hood 12.

Figures 10A, 10B:
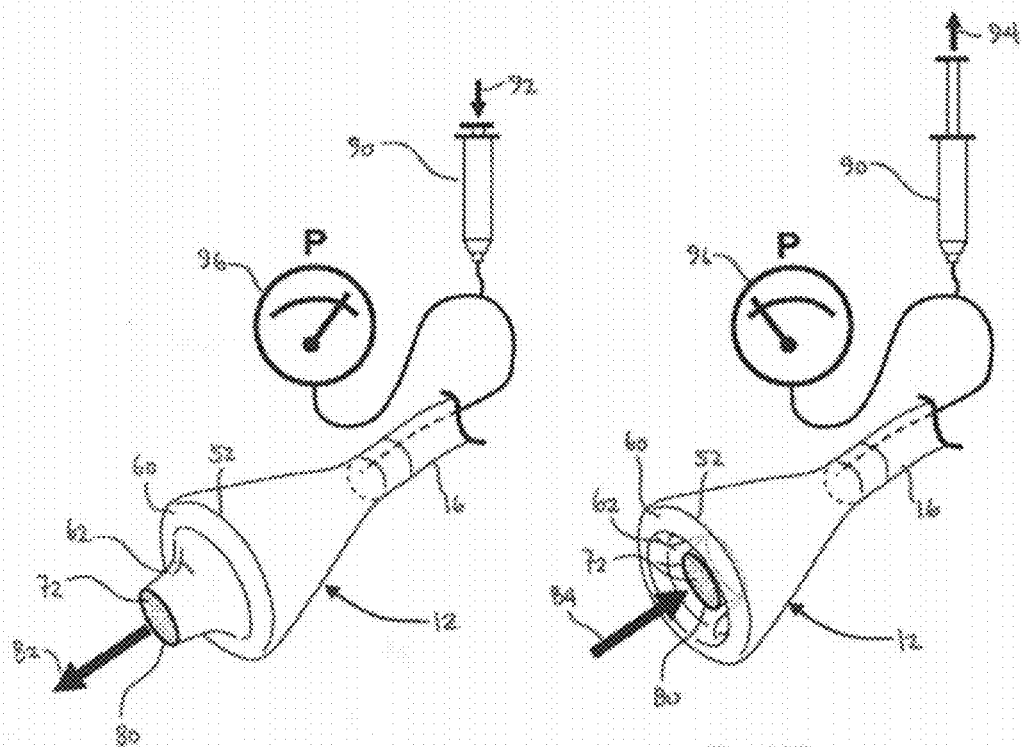
FIGS. 10A and 10B show perspective views of another variation where the open area of the hood may be pressurized or de-pressurized to deploy and retract the elongated feature.

FIGS. 10A and 10B show perspective views of another variation for deploying 82 and/or retracting 84 the elongated feature 62. In this variation, the elongated feature 62 may incorporate fluid permeable feature 72 such that when the interior of the hood 12 is pressurized to create an internal positive pressure (e.g., via a depressed 92 plunger in syringe 90, a pump, or any other pressurized fluid source) as indicated by pressure gauge 96, the elongated feature 62 may be urged to extend or deploy 82 from the hood 12 despite some fluid leakage through permeable feature 72. Similarly, the hood interior may be de-pressurized (e.g., by the retraction of plunger 94) as indicated by the decreased pressure on gauge 96 to create an internal negative and/or reduced pressure that effectively retracts 84 the elongated feature 62 proximally into the open area of the hood 12. The elongated feature 62 may be configured to deploy and/or retract at predetermined pressures.

Figures 11A, 11B:
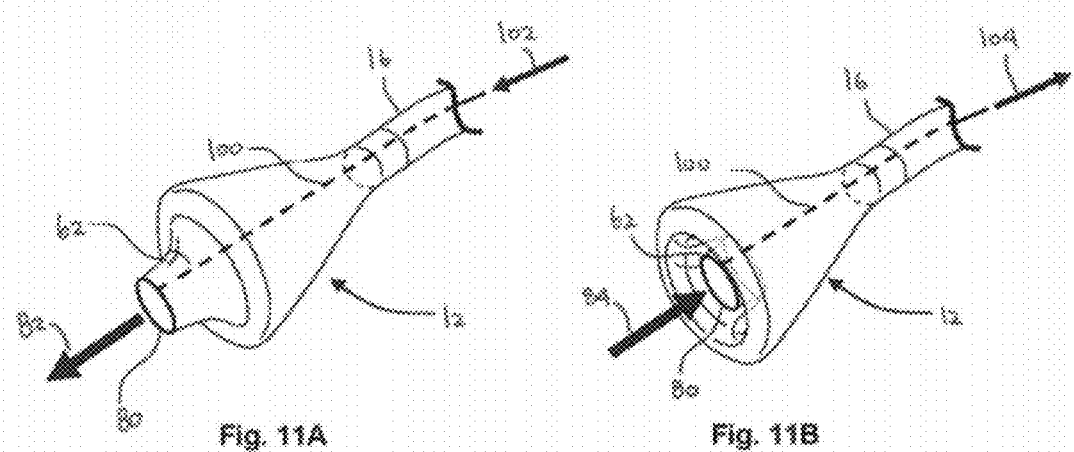
FIGS. 11A and 11B show perspective views of another variation with an internal rigid member which may be actuated to deploy or retract axially the elongated feature.

FIGS. 11A and 11B show perspective views of another variation of hood 12 which incorporates a relatively rigid internal support member 100 attached to stiffening member 80 which may be pushed or pulled axially through catheter 16 to impart a force to the stiffening member 80. In use, the internal support member 100 may be selectively pushed relative to the catheter 16 and hood 12 to deploy 82 elongated feature 62. Similarly, support member 100 may be selectively pulled to retract 84 the elongated feature 62. Alternatively, support member 100 may be actuated to one or more intermediate positions to maintain the elongated feature 62 at some partially deployed or retracted configuration.

Figure 12A:
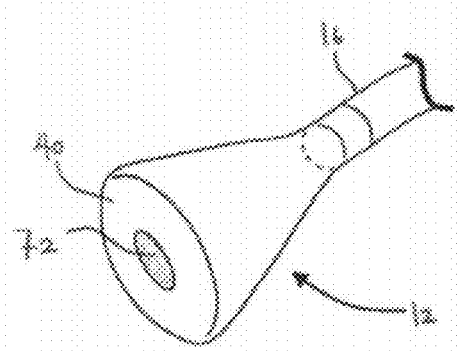
FIGS. 12A and 12B show perspective views of another variation incorporating a permeable material over the aperture.
Figure 12B:
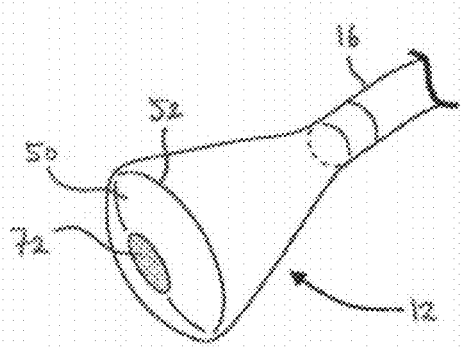
Figure 13A:
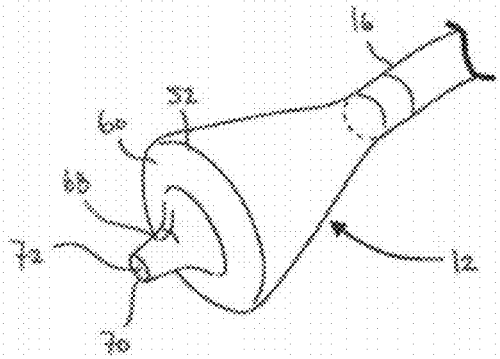
FIG. 13A shows a perspective view of another variation with an elongated feature and a permeable material over the aperture.

In any of the variations shown and described herein, the permeable feature 72 may be optionally incorporated over the aperture with or without the elongated features to provide additional rigidity to the hood shape while being partially pressurized with fluid for flushing/irrigating. This added rigidity may minimize distortions and deformations of the hood aperture and therefore facilitate an even energy density distribution during ablation. FIG. 12A shows a perspective view of hood 12 having distal membrane 40 with permeable feature 72 covering the aperture. FIG. 12B shows a perspective view of hood 12 having the rounded or extended distal membrane 50 also having permeable feature 72 covering the aperture. FIG. 13A shows a perspective view of hood 12 having the elongated feature 68 also having permeable feature 72 covering the aperture.

Figure 13B:
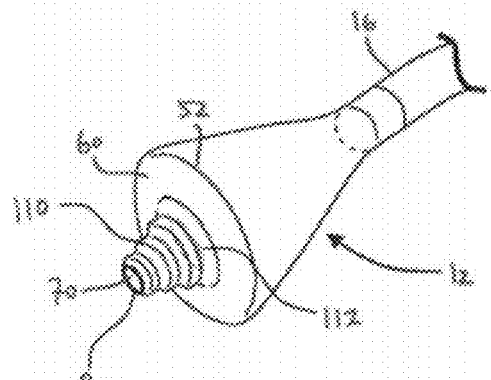
FIG. 13B shows a perspective view of another variation of an elongated feature having annular corrugations and internal feature that limits travel.

FIG. 13B shows a perspective view of another variation of hood 12 having a tapered elongated feature 110 which is comprised of annular corrugations that allow it to compress or expand in an axial direction by allowing the corrugations to roll or intussuscept within one another and compress. The annular corrugations may compress into a stable cylindrical-like structure in order to minimize kinks, folds, wrinkles or other unwanted geometries that would otherwise impede fluid flow or cause a visualization obstruction.

The elongated feature 110 may be tapered and may further optionally incorporate a stiffening member 80 around its aperture 70, as previously described, to provide additional structural rigidity. A permeable feature may also be optionally incorporated as well over aperture 70, if so desired. Additionally, an optional stiffening structure 112 (such as a ring, hoop, etc.) may be positioned within the open area of the hood 12 proximal to the elongated feature 110 and proximal to the aperture 70 to limit the degree of invagination that the elongated feature 110 collapses into the hood open area, as shown in FIG. 13B. This may help control the "snap" or biphasic nature of the collapsing elongated feature 110 and prevent uncontrolled or unwanted movement.

Figure 13C:
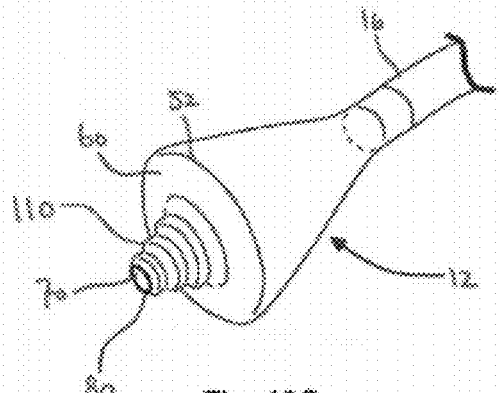
FIG. 13C shows a perspective view of another variation of an elongated feature that has annular corrugations similar to FIG. 13B but without the internal feature.
Figure 13D:
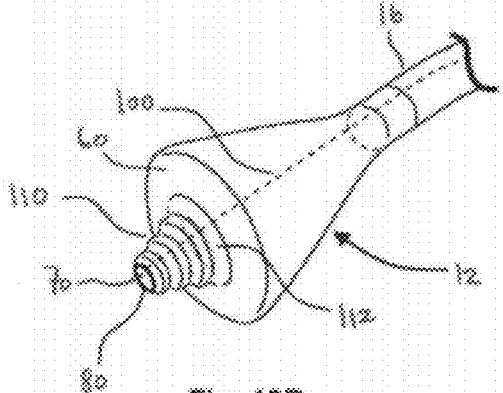
FIG. 13D shows a perspective view of another variation of an elongated feature that has annular corrugations and an internal actuation member which enables the controlled distal displacement or retraction of the elongated feature.

FIG. 13C shows a perspective view of another variation of hood 12 having the corrugated elongated feature 110 but without, the internal stiffening structure 112 which may simplify the overall design and provide the ability to store extra material within the open area of the hood 12, especially for small hood volumes and form factors that are desirable for reaching especially small, tight, or constrained regions of target tissue. FIG. 13D shows a perspective view of another variation of hood 12 having the elongated feature 110 but with support member 100 attached to the stiffening member 80 to selectively retract or deploy the elongated feature 110.

Figures 14A, 14B:
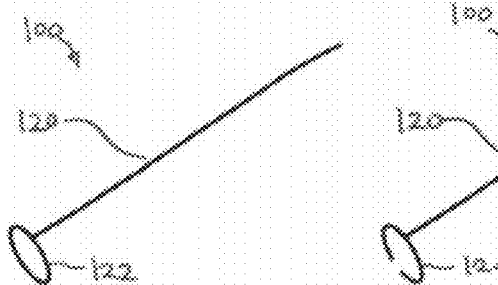
FIGS. 14A and 14B show perspective views of various rigid members.

FIGS. 14A and 14B show examples of support member 100 as having an elongate and flexible wire-like member 120 and the attached stiffening member where the stiffening member may be shaped as a complete annular ring 122 or as a discontinuous substantially circular ring 124. Although illustrated as circular rings, the stiffening member may be formed of any shape or geometry as practicable. Moreover, the support member may be made from a polymer or metal and can be substantially stiff or soft but rigid enough to transmit force.

Figures 15A, 15B:
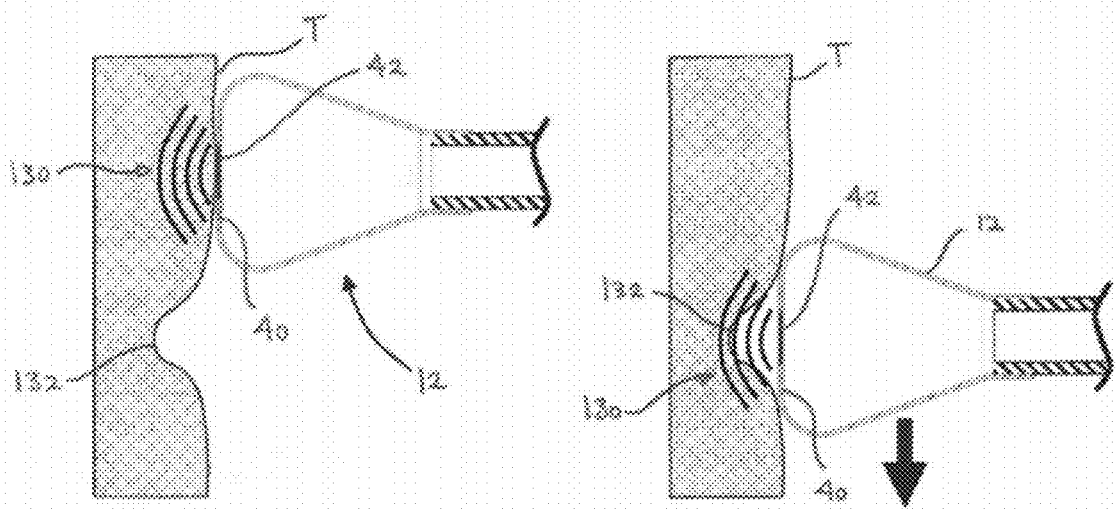
FIGS. 15A and 15B show cross-sectional side views of a hood delivering energy to a tissue sample where the aperture is in intimate contact against the tissue surface and at a distance from an uneven tissue region.

For comparison, FIG. 15A and FIG. 15B illustrate one example of how a hood 12 may be used along a tissue region having an uneven or invaginated surface to deliver RF energy (or any other energy) to a tissue without the use of an elongated feature. As previously described, energy may be conducted through the clearing fluid (e.g., saline) introduced through the hood and passed through the hood aperture 42 and into the underlying tissue either prior to, during, or after visualization of the tissue region. With the distal membrane 40 and aperture 42 positioned against the tissue surface T, the energy 130 may be delivered through the clearing fluid and into the tissue. As the hood 12 is moved along the tissue surface or repositioned at another location, such as an uneven invaginated tissue region 132 shown in FIG. 15B, the delivered energy 130 may pass through the aperture 42 which may be positioned at a distance from the underlying invaginated tissue 132 potentially resulting in a reduction of energy and drop in efficiency of the ablative energy reaching the target tissue.

Figure 16A:
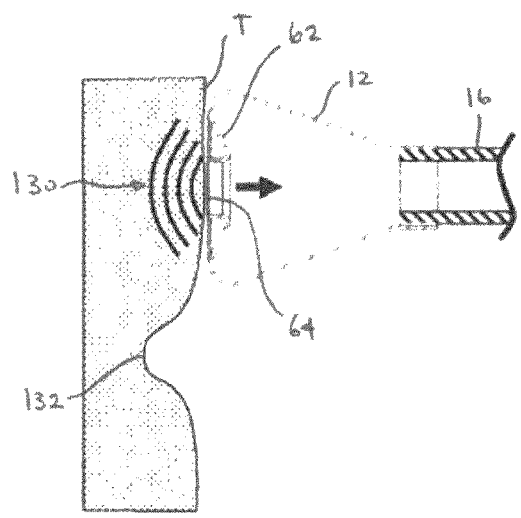
FIGS. 16A and 16B show cross-sectional side views of a hood delivering energy through an elongated feature which is retracted when positioned against a region with a relatively flat surface and a region with an uneven tissue surface.
Figure 16B:
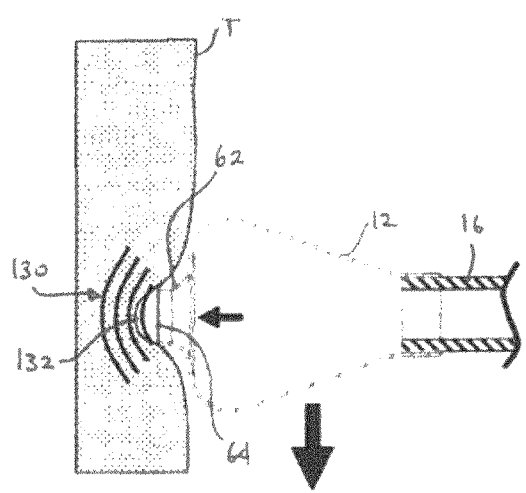

Turning now to FIGS. 16A and 16B, an example is illustrated where the aperture 64 of the hood 12 may be maintained in intimate contact against the tissue surface T when a retracted elongated feature 62 is withdrawn into the open area of the hood when visualizing and/or treating a relatively flattened region of tissue T. The energy 130 may delivered to the tissue with maximum efficacy and efficiency due to the elongated feature 62 being able to "collapse" and invaginate (fold) within the open area of the hood 12. The elongated feature 62 may be maintained in its collapsed configuration by maintaining the hood 12 against the tissue surface or utilizing any of the reconfiguration mechanisms described herein.

As the hood 12 is moved to an invaginated tissue region 132, as shown in FIG. 16B, elongated feature 62 may be allowed to extend from the open, area of the hood 12 and project distally at least partially or fully into the invaginated tissue region 132 to reposition its aperture 64 into intimate or direct contact against the invaginated tissue. The energy 130 may then be delivered to the tissue through aperture 64 with maximum efficacy and efficiency.

Figure 17A:
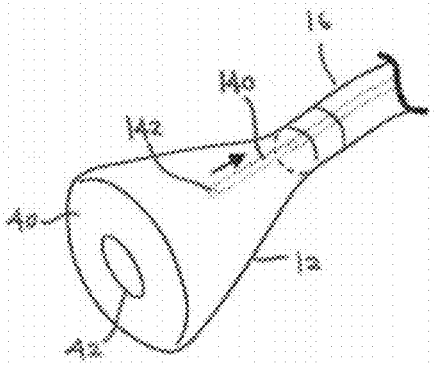
FIGS. 17A to 17C illustrate perspective views of a hood having an electrode instrument which may be advanced distally through the hood aperture.
Figure 17B:
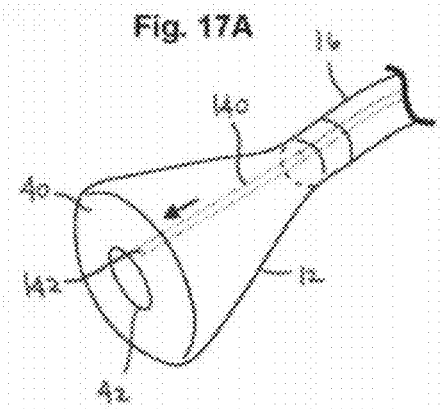
Figure 17C:
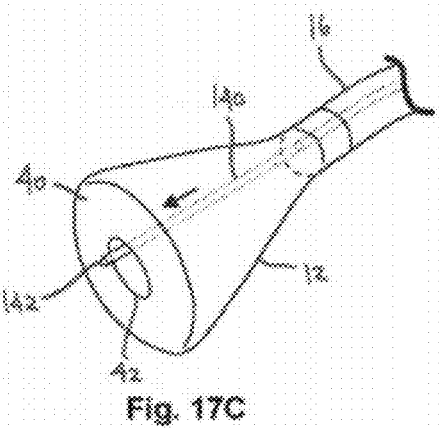

In yet another variation, alternatively and/or additionally to the elongated feature, an electrode tipped shaft or catheter may be advanced or retracted through the catheter 16 and hood open area to deliver energy either through the hood aperture 42 or distal to the aperture 42. FIGS. 17A and 17B show perspective views of hood 12 with an electrode 142 positioned at a distal end of shaft or catheter 140 for delivering RF energy that can be advanced distally within the hood to control/adjust/alter energy delivery through the hood aperture 42. FIG. 17C shows how electrode 142 may be advanced distally such that the electrode 142 is passed through aperture 42 and outside the distal membrane 40 such that energy can be delivered to tissue regions beyond the face of the hood or in order to directly contact the target tissue.

Figure 18A:
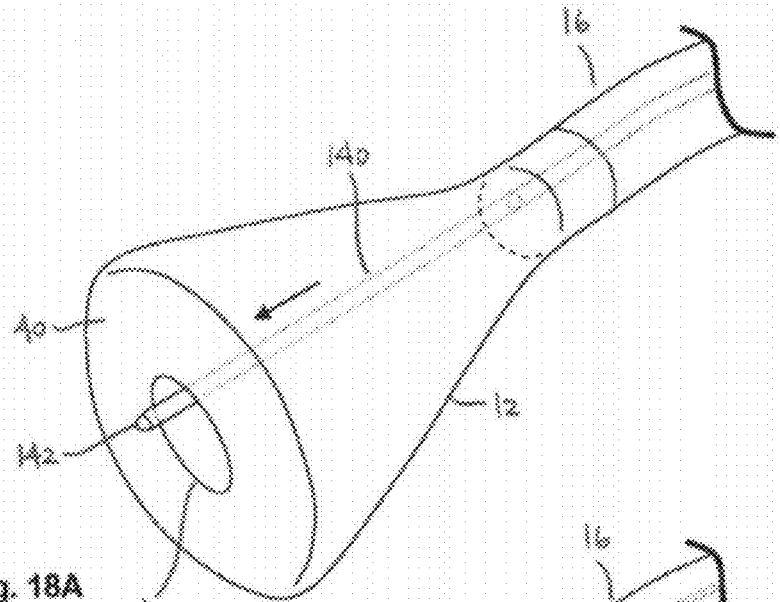
FIGS. 18A to 18E illustrate perspective views of a hood having an electrode instrument with a retractable sheath.
Figure 18B:
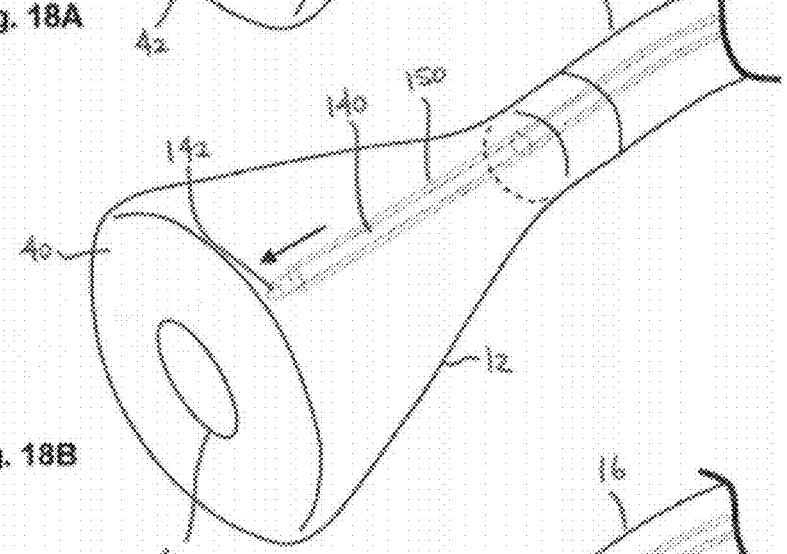
Figure 18C:
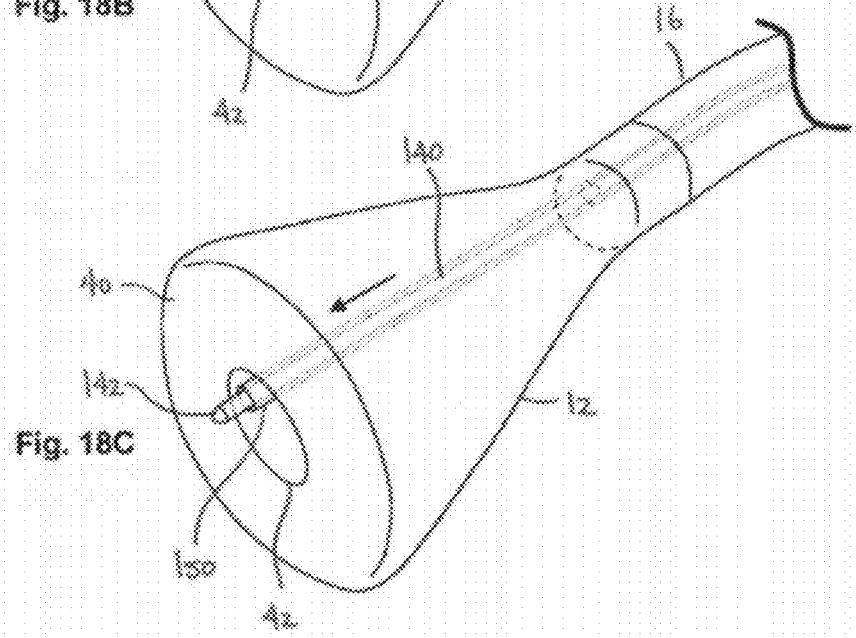

In yet another variation, electrode 142 having a slidable sheath 150 can be advanced through the hood open area where a position of the sheath 150 can be independently controlled relative to the electrode 142, as shown in FIGS. 18A to 18C. By adjusting the position of sheath 150 relative to the electrode 142 location, the amount of exposed surface area of electrode 142 can be controlled to adjust the output energy density given a certain power setting to adjust the lesion formation characteristics. Furthermore, the entire assembly can be placed in any position within the hood 12 or outside of the hood 12 such that the RF energy delivery can be customized to achieve a desired lesion shape, area and/or depth by altering the energy density exposed to the target tissue. The position of the sheath 150 relative to the electrode 142 and to aperture 42 can be adjusted proximally and distally by either controlled, indexed, and/or defined displacements of the delivery system in order to prevent an injury due to unwanted penetration into the tissue surface.

FIG. 18A shows an example of how electrode 142 and shaft 140 may be advanced distally through hood 12 with sheath 150 retracted within the catheter 16. FIG. 18B shows a perspective view of electrode 142 retracted proximally within the hood open area but with the sheath 150 partially advanced to control and/or focus energy delivery by covering a portion of the electrode 142 (depending on the electrode shape, design or configuration). FIG. 18C shows another example of electrode 142 that is advanced distally past aperture 42 but with sheath 150 partially advanced as well to control and/or focus energy delivery by covering a portion of the electrode 142.

Figure 18D:
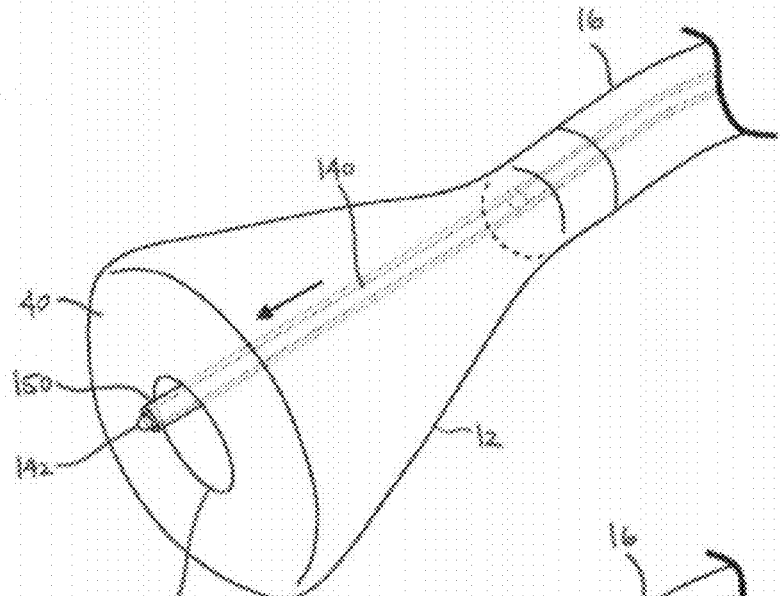
Figure 18E:
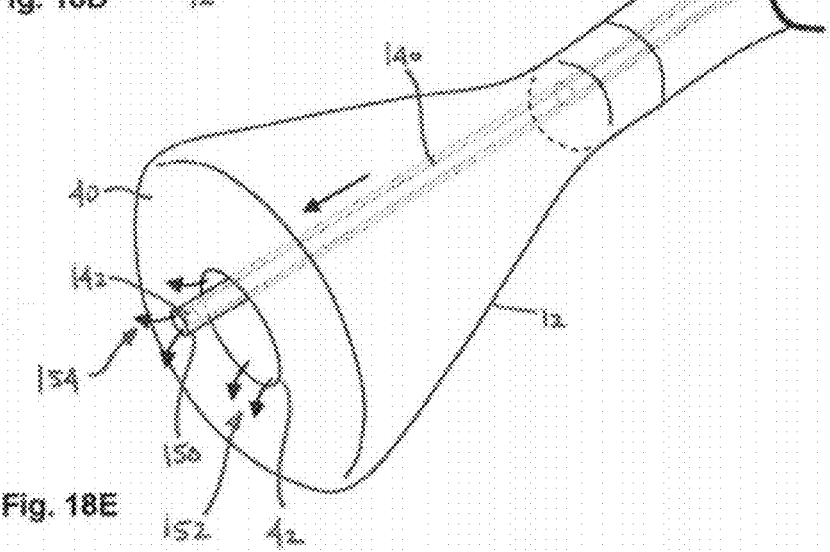

FIG. 18D shows a perspective view of electrode 142 and sheath 150 advanced together through hood 12 and distally past aperture 42. FIG. 18E illustrates electrode 142 with sheath 150 advanced beyond of the electrode 142. By covering the electrode 142, the energy emitted from the electrode 142 may be focused to a narrow region of target tissue, either in a tissue contact or non-contact configuration, by further passing an electrolytic fluid 154 not only through hood aperture 42 but also through sheath 150 and past electrode 142 as well.

FIG. 19A illustrates a cross-sectional side view of hood 12 with electrode 142 advanced past the hood aperture 42 and in proximity with the tissue region T for delivering the energy directly to the tissue T. Even with the distal membrane 40 of hood 40 removed from contact with the tissue T, energy 130 may be delivered to the tissue. FIG. 19B shows another example where electrode shaft 140 and sheath 150 may be retracted proximally into the open area of the hood 12. In this configuration, energy 130 may be delivered through the clearing fluid passed through aperture 42 and directly to the tissue T with distal membrane 40 in contact or adjacent to the tissue surface.

FIG. 20A shows a side view of hood 12 in another example where electrode 142 may be advanced distally of aperture 42 and in proximity against the tissue surface T with sheath 150 at least partially covering electrode 142. Due to the limited area of exposed electrode 142 and the close proximity to the tissue T, the energy 130 may be delivered in a more focused region to create a narrower region of ablated tissue. FIG. 20B shows another example with the covered electrode 142 positioned within the hood 12 while delivering the energy 130 through the aperture to the target tissue T. Due to the covered electrode and the retracted position, the delivered energy 130 may treat a larger area of tissue than that shown in FIG. 20A.

In utilizing the electrode and sheath 150, different electrode configurations may be used depending upon the desired application. FIG. 21A shows a cross-sectional side view of an electrode having a constant area. FIG. 21B shows an electrode shaft 160 having an expandable tip member or members 162 initially constrained in a low-profile configuration within the sheath 150. FIG. 21C shows the electrode tip 162 in a deployed configuration beyond the cover where the tip may be expanded in two or more members to increase the surface area of the exposed electrode and provide another mechanism of adjusting the delivered energy density.

In utilizing any of the assemblies described herein, regions of tissue to be visualized or treated may be obstructed by various anatomy such as trabeculae which may prevent the hood 12 from advancing or contacting the tissue to be visualized or treated. An example is illustrated in FIGS. 22A and 22B which show cross-sectional side views of a hood 12 which may deliver energy 130 to underlying tissue T which is relatively flat allowing for direct apposition of the aperture 42 against or in proximity to the tissue surface. As the hood 12 is moved across an uneven region of tissue 132 which is obstructed by trabeculae 170, visualization and/or energy delivery may be hindered due to poor energy density or energy fall-off beyond the hood aperture 42, as shown in FIG. 22B.

Using any of the variations described herein, obstructed tissue may still be effectively treated. One example is shown in the cross-sectional side views of FIGS. 23A and 23B. As shown, elongated feature 62 may be retracted within the hood open area to visualize and/or treat the underlying tissue T along relatively flattened areas, as shown in FIG. 23A. However, as the hood 12 encounters, e.g., trabeculae 170 within a region of uneven tissue 132, the elongated feature 62 may be deployed or extended to fit within the trabeculae 170 such that the aperture 64 is closer to the targeted tissue to more effectively deliver a higher energy density for more efficient and effective ablation.

Figure 24:
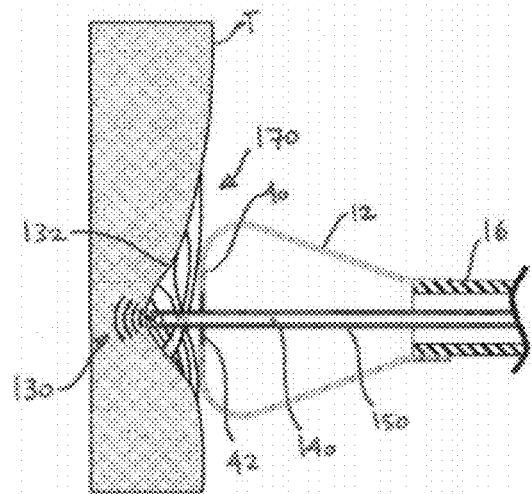
FIG. 24 shows a cross-sectional side view of an electrode instrument fitted or interdigitated between the trabeculae and to impart focused energy to the target tissue.

FIG. 24 shows another example where the electrode shaft 140 and/or sheath 150 may be advanced distally past the aperture 42 and fitted or interdigitated between the trabeculae 170 to impart focused energy 130 to the target tissue.

Figure 25A:
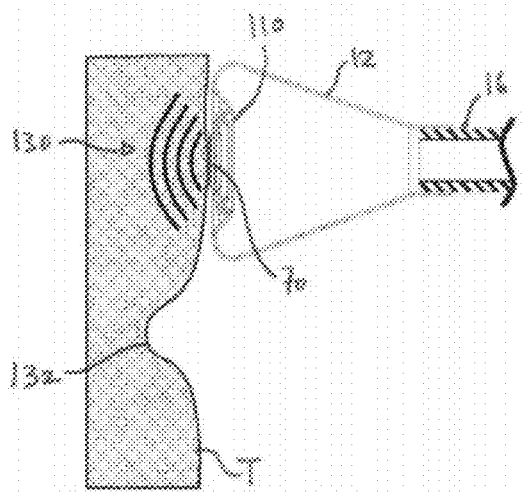
FIGS. 25A and 25B show cross-sectional side views of an elongated feature extended distally as it nests within an invagination in the target tissue surface.
Figure 25B:
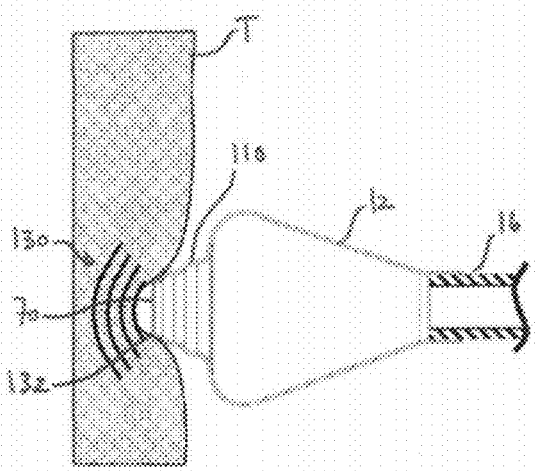

FIGS. 25A and 25B show another example where elongated feature 110 which is corrugated may be collapsed within the hood open area when placed against a relatively flat target tissue surface T. When advanced over an uneven region or tissue 132, the corrugated elongated feature 110 may be extended distally to nest within the invagination in the target tissue surface. Due to the resiliency in the material of the elongated feature and/or by using an internal rigid member (as described above), the elongated feature 110 can fit within the pocketed feature. Even when not being able to reach the deepest recesses of the invagination, the delivered energy density can remain high due to the captured/contained volume of energized fluid which reduces energy losses to the rest of the fluid environment. The tissue can still be cooled to prevent excessive ablation and/or bubble formation by flushing the contained region with the clearing fluid at a relatively lower temperature.

Figure 26A:
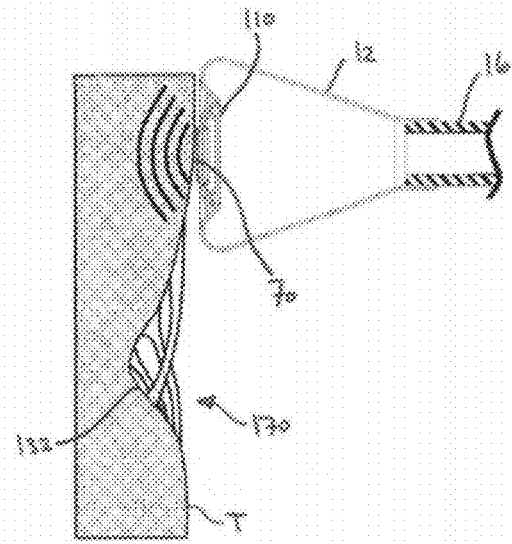
FIGS. 26A and 26B show cross-sectional side views of a hood with a corrugated elongated feature extended distally to nest within a trabeculated invagination in the target tissue surface.
Figure 26B:
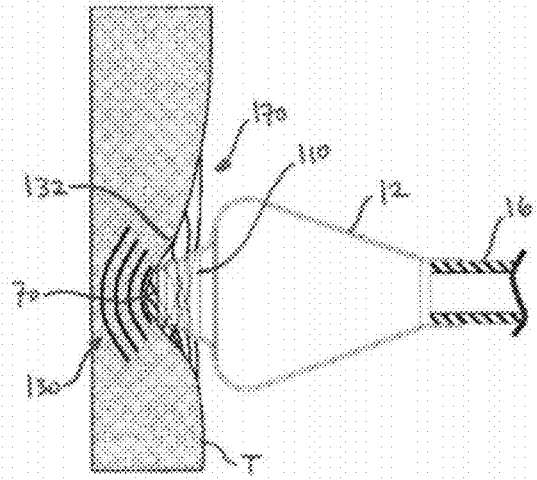
Figure 27A:
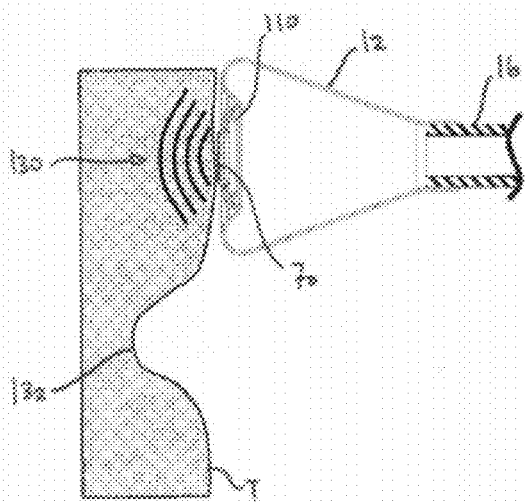
FIGS. 27A and 27B show cross-sectional side views of a hood with a corrugated elongated feature extended distally to nest within an invagination in the target tissue surface.
Figure 27B:
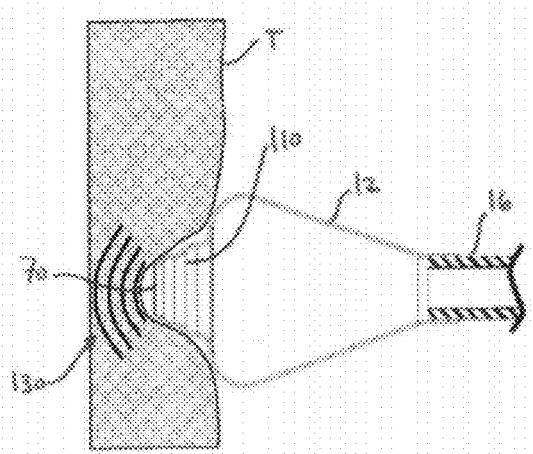

FIGS. 26A and 26B shows yet another example of the elongated feature 110 which may be used to treat a relatively flattened tissue region T when the feature 110 is in a collapsed configuration and then extended when encountering an uneven tissue region 132 even when obstructed, e.g., by trabeculae 170. FIGS. 27A and 27B show another example where the elongated feature 110 may be fully, extended into an uneven region of tissue 132 which is particularly deep to effectively deliver the energy 130 to the underlying invaginated tissue.

Figure 28A:
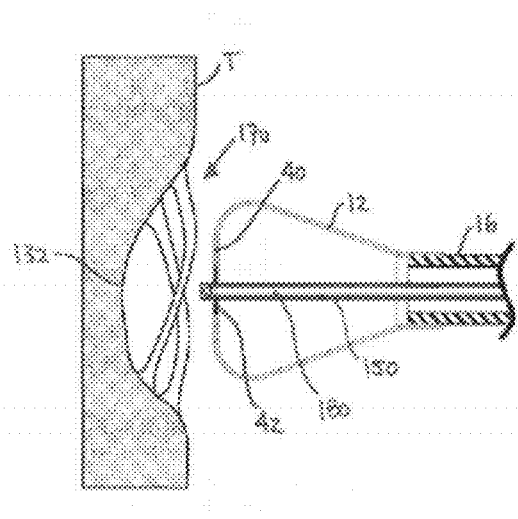
FIGS. 28A to 28E show cross-sectional side views of a hood having an electrode instrument which has a distal portion which is configured with a pre-determined curvature to effectively catch or hook trabeculae which may then be severed to allow for the hood to access the underlying tissue region.
Figure 28B:
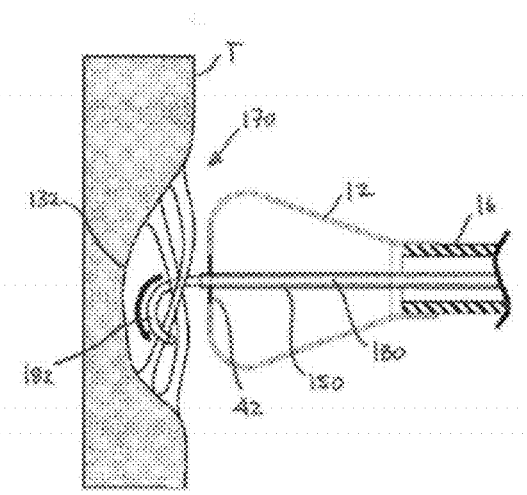
Figure 28C:
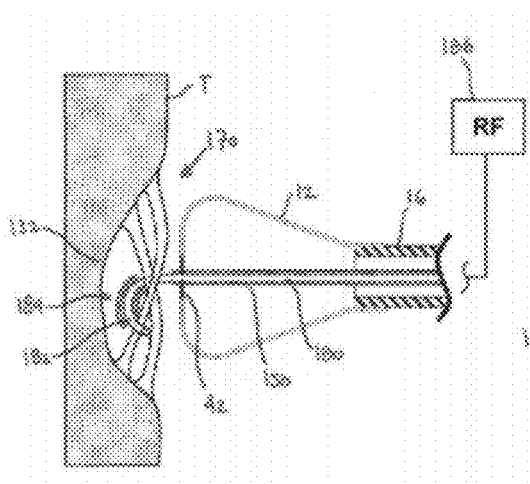

FIG. 28A shows a cross-sectional side-view of another variation of an electrode instrument 180 which may be advanced with an optional sheath 150 through the interior of the hood 12 and distally through the aperture 42 for advancement into an uneven tissue region 132 obstructed, e.g., with trabeculae 170. As the electrode shaft is advanced relative to sheath 150 or hood aperture 42, a distal region 182 of the electrode instrument may be configured to take a pre-set curve in order to effectively catch, harness, or hook the trabeculae 170, as shown in FIG. 28B. With the curved distal region 182 interdigitated within the trabeculae 170, the electrode may be energized, e.g., with RF energy 184 via an RF generator source 186 such that the distal region 182 may effectively cuts or sever the trabeculae 170 or other anatomical structure in order to create sufficient space for the hood 12 to effectively enter the tissue region 132, as shown in FIG. 28C. In other variations, the distal region 182 may alternatively incorporate exposed sharp blade edges to enable the cutting action.

Figure 28D:
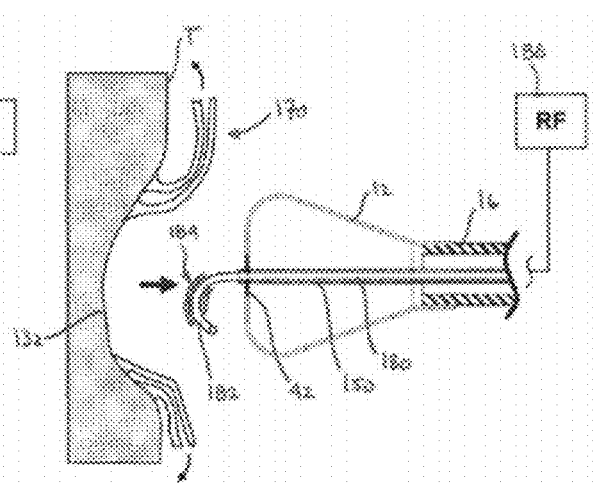
Figure 28E:
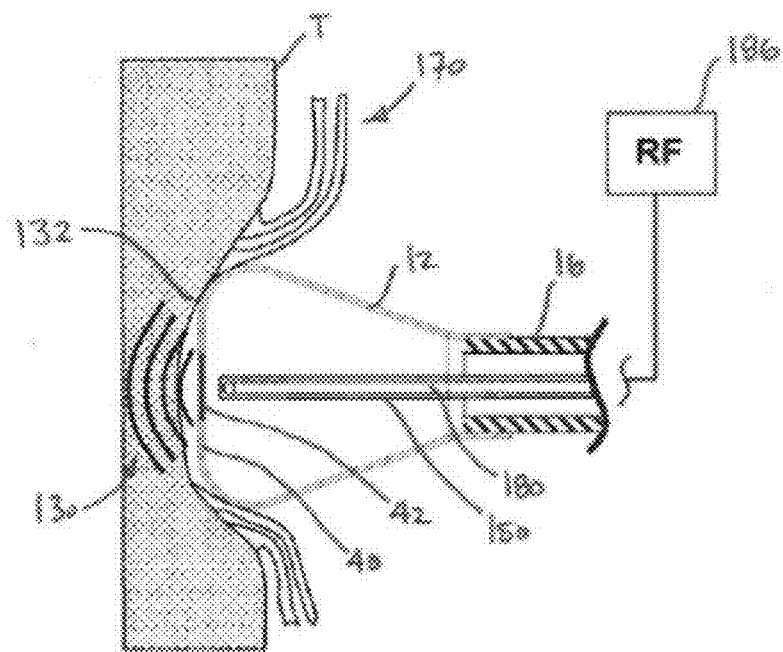

With the energized distal region 182, the trabeculae 170 may be severed and the electrode 182 may be retracted proximally into the hood 12, as shown in FIG. 28D. FIG. 28E shows a cross-sectional side view of hood 12 advanced distally into intimate contact within the uneven target tissue region 132. The exposed electrode tip of the shaft or catheter can then be energized to ablate the targeted tissue through the aperture 42.

Figure 29:
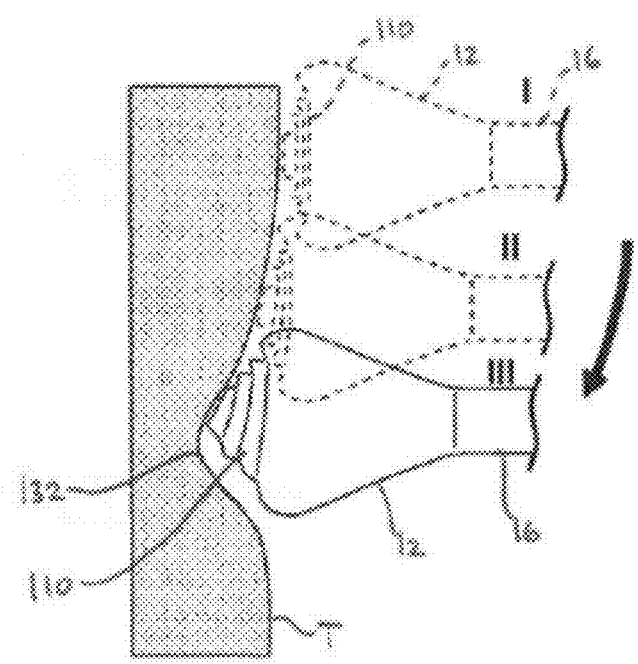
FIG. 29 illustrates an example of how a hood having a corrugated elongated feature may maintain contact with the target tissue as the hood is translated along a curved surface.

In yet another example of use for hood 12 having an elongated feature which is corrugated, FIG. 29 illustrates an example of how the hood aperture 42 may be maintained along a tangential (and/or intimate) contact with the target tissue T while the hood 12 is translated along a curved surface. In a first exemplary position, indicated by position (I), elongated feature 110 may be maintained in a collapsed configuration while visualizing and/or treating the underlying tissue. As hood 12 is moved across the tissue surface T, as indicated at position (II) where the underlying tissue surface may begin to curve, elongated feature 110 can accommodate changes in the relative angle between the hood face and the target tissue surface as well as the distance to the target tissue. As the hood 12 is further translated along the varied (variable) target tissue surface T, the elongated feature 110 may further adjust automatically without necessitating that the entire hood 12 change its overall orientation in order to maintain a good physical proximity of the hood aperture 42 with the target tissue T to ensure efficient and effective ablation of the tissue by minimizing large electrolyte leaks that can also disperse ablative energy.

FIG. 30A shows a perspective view of hood 12 with corrugated elongated feature 110 that may incorporate an optional internal feature or ridge 112 within the hood 12 that limits the excursion of the elongated feature 110 as it is compressed internally within the hood 12 open area. FIGS. 30B and 30C illustrate internal feature or ridge 112 configured in this example as a circumferential annular ring that limits the excursion of the collapsed feature 110 as it retracts proximally into hood 12. Feature or ridge 112 can also limit the snapping or popping between deformed states that may occur as the corrugated regions fold over each other as they are compressed.

Figure 31A:
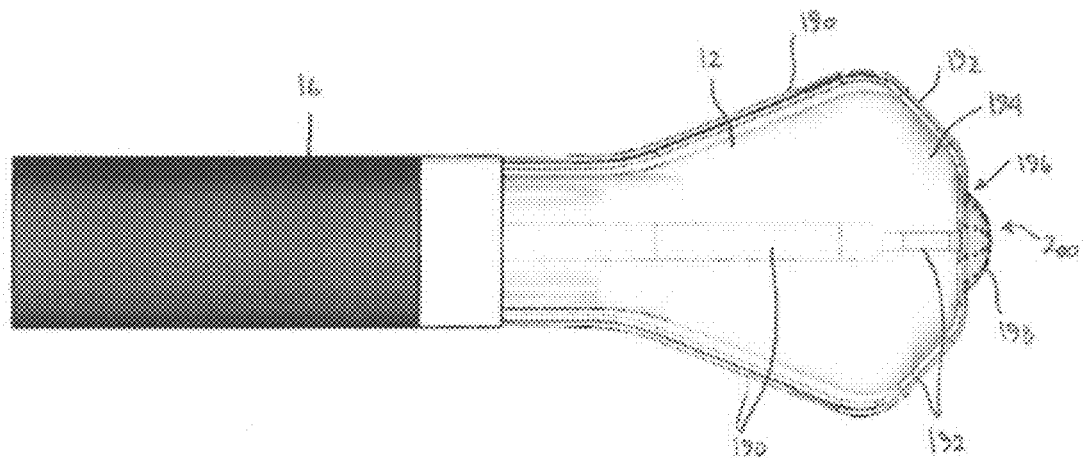
FIGS. 31A and 31B show side and perspective views of yet another variation where the hood may further incorporate an optional porous or fluid dispersing feature over aperture.
Figure 31B:
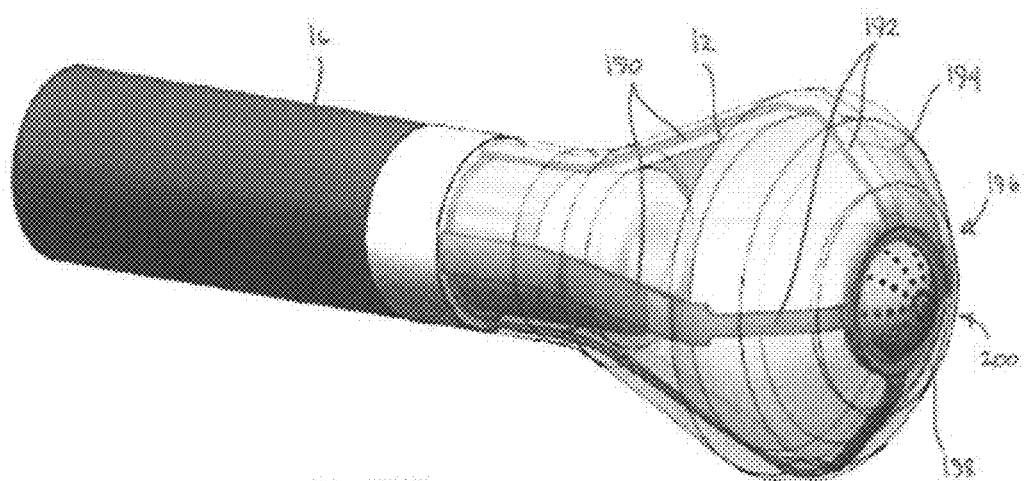

FIGS. 31A and 31B show side and perspective views of yet another variation where hood 12 may further incorporate an optional porous or fluid dispersing feature over aperture 196. In this example, the porous or fluid dispersing feature 198 may generally comprise a cap-like or domed structure which curves distally beyond the hood face in an arcuate manner. The fluid dispersing feature 198 may define one or more (e.g., a plurality) of openings 200 over the feature 198 which allow for the free passage of the clearing fluid through the feature 198 in a dispersed manner much like a shower head. The feature 198 may be energized or charged via one or more connections, e.g., through support struts 190, to provide for the application of energy through the clearing fluid as the fluid is dispersed through the feature 198. Accordingly, feature 198 may be comprised of a metallic or electrically conductive material. Alternatively, the clearing fluid may be energized via an electrode within the hood 12 interior and then pass through the dispersing feature 198 to the underlying tissue.

Hood 12 may further define a distally curved portion 194 supported, e.g., by distal support struts 192 connected to corresponding support struts 190. With the incorporated dispersing feature 198, the clearing fluid may be dispersed in an even manner from the hood 12 and over the underlying tissue to provide a more even distribution of energy, e.g., for ablation of the tissue.

Figure 32A:
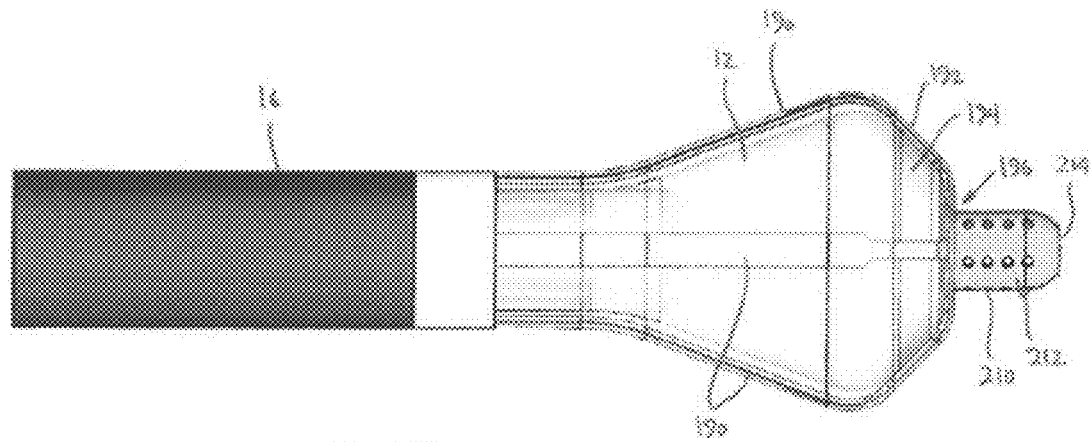
FIGS. 32A and 32B show side and perspective views of yet another variation of a hood assembly incorporating a fluid dispersing feature where the feature may be configured as a tubular or cylindrical structure which covers the aperture and further extends distally from the hood.
Figure 32B:
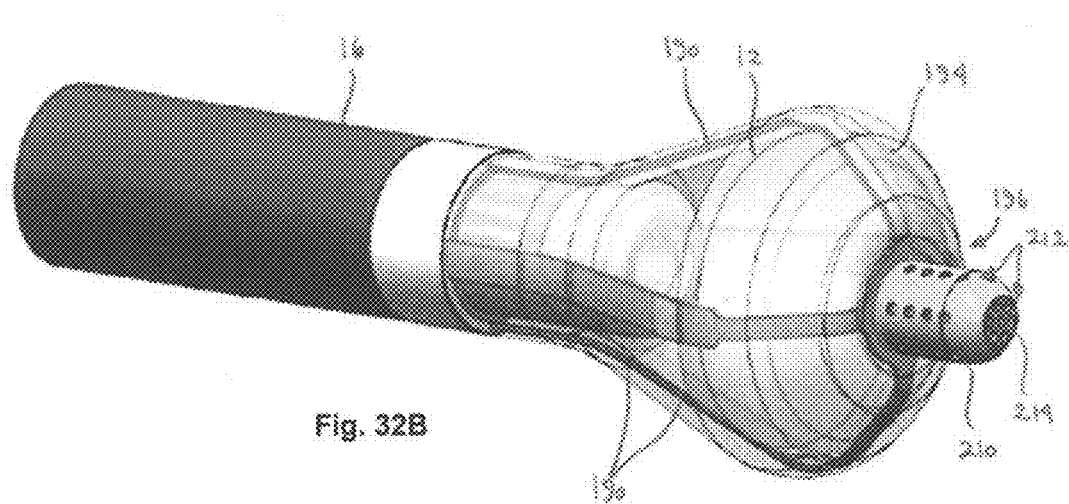

FIGS. 32A and 32B show side and perspective views of yet another variation of a hood assembly incorporating a fluid dispersing feature where the feature 210 may be configured as a tubular or cylindrical structure which covers the aperture 196 and further extends distally from hood 12. With the dispersing feature 210 configured as a cylindrical structure, feature 210 may contact the underlying tissue along its side surfaces or within uneven anatomy to more evenly disperse the energized clearing fluid. Thus, feature 210 may define one or more openings along its side 212 or along its distal surface 214 through which the clearing fluid may disperse evenly from the hood 12. As above, while dispersing feature 210 may be comprised of a metallic or electrically conductive material for energizing the clearing fluid directly, it may be comprised of a non-electrically conductive material for passing the clearing fluid which may already by energized by another electrode within the hood interior.

The applications of the disclosed invention discussed above are not limited to certain treatments or regions of the body, but may include any number of other applications as well. Modification of the above-described methods and devices for carrying out the invention, and variations of aspects of the invention that are obvious to those of skill in the arts are intended to be within the scope of this disclosure. Moreover, various combinations of aspects between examples are also contemplated and are considered to be within the scope of this disclosure as well.

The invention claimed is:

1. An apparatus for ablating a tissue region having irregular anatomy, comprising:
    an elongate catheter having a distal end and a flexible length; and
    a hood attached to the distal end and having a low-profile shape and a deployed shape, wherein the hood includes a distal edge and defines an open area when in the deployed shape which is in fluid communication with an environment external to the hood through an aperture of a distal membrane coupled to the distal edge of the hood,
    wherein the distal membrane includes a distal surface extending between the distal edge of the hood and a proximal end of an elongated conduit feature, the elongated conduit feature extendable distally from the distal surface between a collapsed configuration and an extended configuration and having a smaller outer diameter than the distal edge of the hood in both a fully extended configuration and the collapsed configuration, wherein the elongated conduit feature has a distal end that defines the aperture having a diameter which is less than a diameter of the hood such that a purging fluid introduced into the open area from the catheter is urged through the aperture of the elongated conduit feature and into the environment.

2. The apparatus of claim 1 further comprising an imaging element positioned within or adjacent to the hood for visualizing the tissue region distal to the aperture.

3. The apparatus of claim 1 further comprising one or more struts along the hood which provide structural support.

4. The apparatus of claim 1 wherein the hood is configured to self-expand.

5. The apparatus of claim 1 further comprising a permeable feature over the aperture.

6. The apparatus of claim 1 wherein the elongated conduit feature is tapered between the proximal and distal ends.

7. The apparatus of claim 1 further comprising a rigidizing member around the aperture.

8. The apparatus of claim 1 further comprising an actuation member connected to the aperture for deploying or retracting the elongated conduit feature relative to the hood.

9. The apparatus of claim 1 wherein the elongated conduit feature comprises a plurality of annular rings.

10. An apparatus for ablating a tissue region having irregular anatomy, comprising:
    an elongate catheter having a distal end and a flexible length;
    a hood projecting distally from the distal end, where the hood includes a distal edge and is configurable between a low-profile shape and a deployed shape where the hood defines an open area in fluid communication with the catheter,
    a distal barrier including an inner boundary and an outer boundary coupled to the distal edge of the hood; and
    an elongate conduit projection including a proximal end coupled to the inner boundary of the distal barrier, the elongate conduit projection extendable distally from the distal barrier between a collapsed configuration and a deployed configuration and having a smaller outer diameter than the distal barrier in both a fully deployed configuration and the collapsed configuration, wherein the elongate conduit projection has a distal end that defines an opening which allows for fluid communication between the open area and an environment external to the hood.

11. An apparatus for ablating a tissue region having irregular anatomy, comprising:
    an elongate catheter having a distal end and a flexible length;
    a hood projecting distally from the distal end, where the hood includes a distal edge and is configurable between a low-profile shape and a deployed shape where the hood defines an open area in fluid communication with the catheter; and a distal barrier coupled to the distal edge of the hood and comprising a distal surface extending between the distal edge of the hood and a proximal end of an elongate conduit projection having a corrugated membrane extendable between a collapsed configuration and a deployed configuration, the elongate conduit projection having a smaller outer diameter than the distal barrier in both a fully deployed configuration and the collapsed configuration wherein the elongate conduit projection has a distal end that defines an opening which allows for fluid communication between the open area and an environment external to the hood.

12. An apparatus for ablating a tissue region having irregular anatomy, comprising:

an elongate catheter having a distal end and a flexible length;

a hood projecting distally from the distal end, where the hood includes a distal edge and is configurable between a low-profile shape and a deployed shape where the hood defines an open area in fluid communication with the catheter; and a distal barrier coupled to the distal edge of the hood, the distal barrier comprising a distal surface extending between the distal edge of the hood and a proximal end of an elongate conduit projection, the elongate conduit projection extendable between a collapsed configuration and a deployed configuration and having a smaller outer diameter than the distal edge in both a fully deployed configuration and the collapsed configuration, wherein the elongate conduit projection has a distal end that defines an opening which allows for fluid communication between the open area and an environment external to the hood through a porous membrane.

13. An apparatus for ablating a tissue region having irregular anatomy, comprising:

an elongate catheter having a distal end and, a flexible length;

a hood attached to the distal end of the catheter and having a low-profile shape and a deployed shape, wherein the hood includes a distal edge and defines an open area when in the deployed shape;

a barrier coupled to the distal edge of the hood, the barrier comprising a distal surface extending between the distal edge of the hood and a proximal end of an elongated conduit feature, the elongated conduit feature extendable between a collapsed configuration and a deployed configuration and having a smaller outer diameter than the distal edge in both a fully deployed configuration and the collapsed configuration, the elongated conduit feature having a distal end defining an aperture through which the open area is in fluid communication with an environment external to the hood; and an ablation instrument having a curved distal end positionable through the flexible length such that the curved distal end is advanceable through the aperture and into contact against the tissue region.

14. An apparatus for ablating a tissue region, comprising:

an elongate catheter having a distal end and a flexible length;

a hood attached to the distal end and having a low-profile shape and a deployed shape, wherein the hood includes a distal edge and defines an open area which is in fluid communication with an environment external to the hood; and a barrier comprising a distal surface extending between the distal edge of the hood and a proximal end of an elongated conduit feature, the elongated conduit feature extendable between a collapsed configuration and a deployed configuration and having a smaller outer diameter than the distal edge in both a fully deployed configuration and the collapsed configuration, the elongated conduit feature having a distal end defining an aperture through which the open area is in fluid communication with the environment external to the hood; and wherein the elongated conduit feature comprises a fluid dispersing feature over the aperture at the distal end of the elongated conduit feature, the fluid dispersing feature defining a plurality of openings through which a clearing fluid introduced into the open area is purged through the fluid dispersing feature and into the environment.

15. The apparatus of claim 14 wherein the fluid dispersing feature is comprised of an electrically conductive material.

16. The apparatus of claim 14 wherein the fluid dispersing feature comprises a domed structure.

17. The apparatus of claim 14 wherein the fluid dispersing feature comprises a cylindrical structure.

18. The apparatus of claim 14 further comprising an imaging element positioned within or adjacent to the hood for visualizing the tissue region distal to the aperture.

19. The apparatus of claim 14 further comprising one or more struts along the hood which provide structural support.

20. The apparatus of claim 14 wherein the hood is configured to self-expand.

* * * * *